United States Patent [19]
Cottingham et al.

[11] Patent Number: 5,783,148
[45] Date of Patent: Jul. 21, 1998

[54] NUCLEIC ACID AMPLIFICATION METHOD AND APPARATUS

[75] Inventors: Hugh V. Cottingham, Caldwell, N.J.; Allen Reichler, Owings Mills, Md.; Peter Bourdelle, Glen Rock, Pa.

[73] Assignee: Becton Dickinson and Company, Franklin Lakes, N.J.

[21] Appl. No.: 884,331

[22] Filed: Jun. 27, 1997

Related U.S. Application Data

[63] Continuation of Ser. No. 213,304, Mar. 14, 1994, abandoned.

[51] Int. Cl.⁶ .................................................. G01N 21/05
[52] U.S. Cl. .......................... 422/56; 422/58; 422/61; 422/68.1; 422/102; 422/104; 436/86; 436/94; 436/180; 436/501; 436/508; 435/6; 435/91
[58] Field of Search .................. 422/50, 58, 61, 422/68.1, 73, 56, 82.09, 102, 104; 436/63, 86, 94, 180, 501, 508, 807; 435/6, 91, 172.3, 301

[56] References Cited

U.S. PATENT DOCUMENTS

| | | | |
|---|---|---|---|
| 4,018,652 | 4/1977 | Lanham et al. | 195/103.5 |
| 4,055,394 | 10/1977 | Friedman et al. | 23/253 |
| 4,260,392 | 4/1981 | Lee | 23/230 |
| 4,426,451 | 1/1984 | Columbus | 436/518 |
| 4,457,184 | 7/1984 | Shiono | 73/864.11 |
| 4,580,897 | 4/1986 | Nelson et al. | 356/246 |
| 4,596,695 | 6/1986 | Cottingham | 422/58 |
| 4,623,519 | 11/1986 | Cornut et al. | 422/72 |
| 4,673,657 | 6/1987 | Christian | 436/501 |
| 4,714,590 | 12/1987 | Guigan | 422/102 |
| 4,735,502 | 4/1988 | Kaufmann | 356/246 |
| 4,756,884 | 7/1988 | Hillman et al. | 422/73 |
| 4,774,192 | 9/1988 | Terminiello et al. | 436/530 |
| 4,775,515 | 10/1988 | Cottingham | 422/73 |
| 4,883,763 | 11/1989 | Holen et al. | 436/45 |
| 4,902,479 | 2/1990 | Bri kus | 422/72 |
| 4,902,624 | 2/1990 | Columbus et al. | 435/316 |
| 4,965,188 | 10/1990 | Mullis et al. | 435/6 |
| 5,035,996 | 7/1991 | Hartley | 435/6 |
| 5,039,617 | 8/1991 | McDonald et al. | 436/69 |
| 5,061,446 | 10/1991 | Guigan | 422/64 |
| 5,110,552 | 5/1992 | Guigan | 422/64 |
| 5,122,284 | 6/1992 | Braynin et al. | 210/782 |
| 5,141,868 | 8/1992 | Shanks et al. | 435/288 |
| 5,147,606 | 9/1992 | Charlton et al. | 422/56 |
| 5,147,607 | 9/1992 | Mochida | 422/57 |
| 5,147,609 | 9/1992 | Grenner | 422/58 |

(List continued on next page.)

FOREIGN PATENT DOCUMENTS

| | | |
|---|---|---|
| 1304916 | 7/1992 | Canada. |
| 0246760 | 11/1987 | European Pat. Off.. |
| 0381501 | 8/1990 | European Pat. Off.. |
| 0480497 | 5/1992 | European Pat. Off.. |
| 0057110 | 8/1992 | European Pat. Off.. |
| 0585660 | 3/1994 | European Pat. Off.. |
| 9316801 | 9/1993 | WIPO. |
| 9322058 | 11/1993 | WIPO. |
| 9404929 | 3/1994 | WIPO. |

OTHER PUBLICATIONS

C. A. Burdis et al, "Factors Influencing Evaporation From Sample Cups, and Assessment on Analytical Error", *Clinical Chemistry*, vol. 31, No. 13, pp. 1967-1977 (1975).

*Primary Examiner*—Harold Y. Pyon
*Attorney, Agent, or Firm*—David W. Highet, Esq.

[57] ABSTRACT

The present invention relates to an apparatus for performing a biological process and is particularly useful for processes which include amplicon decontamination and nucleic acid amplification steps. The apparatus includes a sample well for introduction and removal of a liquid biological sample, at least one reaction chamber containing dried reagents in fluid communication with the sample well, a pneumatic chamber in pneumatic communication with the reaction chamber and sample well, and a pneumatic port in the pneumatic chamber for connection of the apparatus to a pneumatic aspiration/dispensing means which causes the flow of the liquid sample within the apparatus.

33 Claims, 15 Drawing Sheets

U.S. PATENT DOCUMENTS

| | | | |
|---|---|---|---|
| 5,171,537 | 12/1992 | Wainwright et al. | 422/100 |
| 5,187,084 | 2/1993 | Hallsby | 435/91 |
| 5,188,963 | 2/1993 | Stapleton | 435/299 |
| 5,219,762 | 6/1993 | Katamine et al. | 436/518 |
| 5,229,297 | 7/1993 | Schnipelsky et al. | 436/94 |
| 5,240,844 | 8/1993 | Wie et al. | 435/7.92 |
| 5,256,376 | 10/1993 | Callan et al. | 422/102 |
| 5,288,646 | 2/1994 | Lundsgaard et al. | 436/165 |
| 5,302,348 | 4/1994 | Cusack et al. | 422/73 |
| 5,304,487 | 4/1994 | Wilding et al. | 435/291 |
| 5,312,757 | 5/1994 | Matsuyama et al. | 436/54 |
| 5,364,744 | 11/1994 | Buican et al. | 430/321 |
| 5,378,638 | 1/1995 | Deeg et al. | 436/518 |
| 5,422,270 | 6/1995 | Caspi | 435/284 |
| 5,422,271 | 6/1995 | Chen et al. | 435/287 |
| 5,424,220 | 6/1995 | Goerlach-Graw et al. | 436/568 |

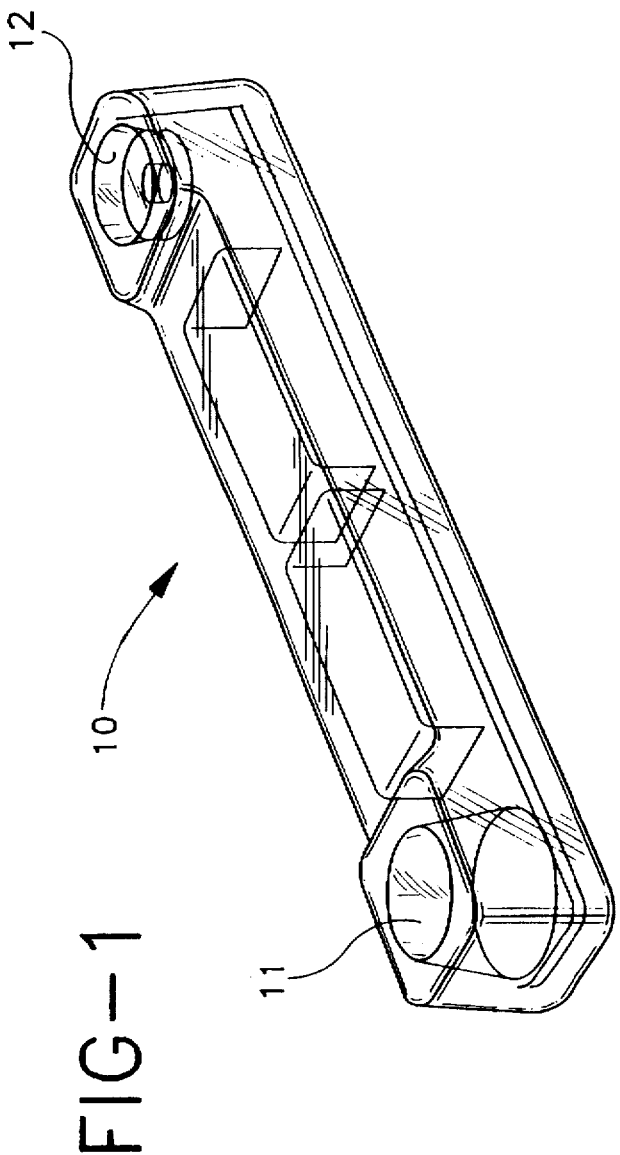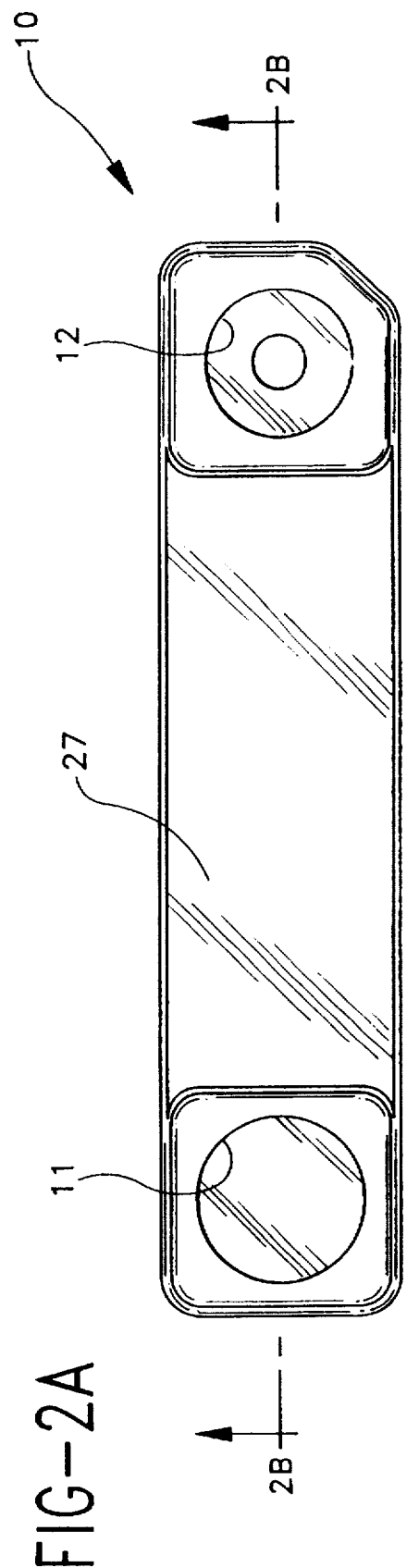

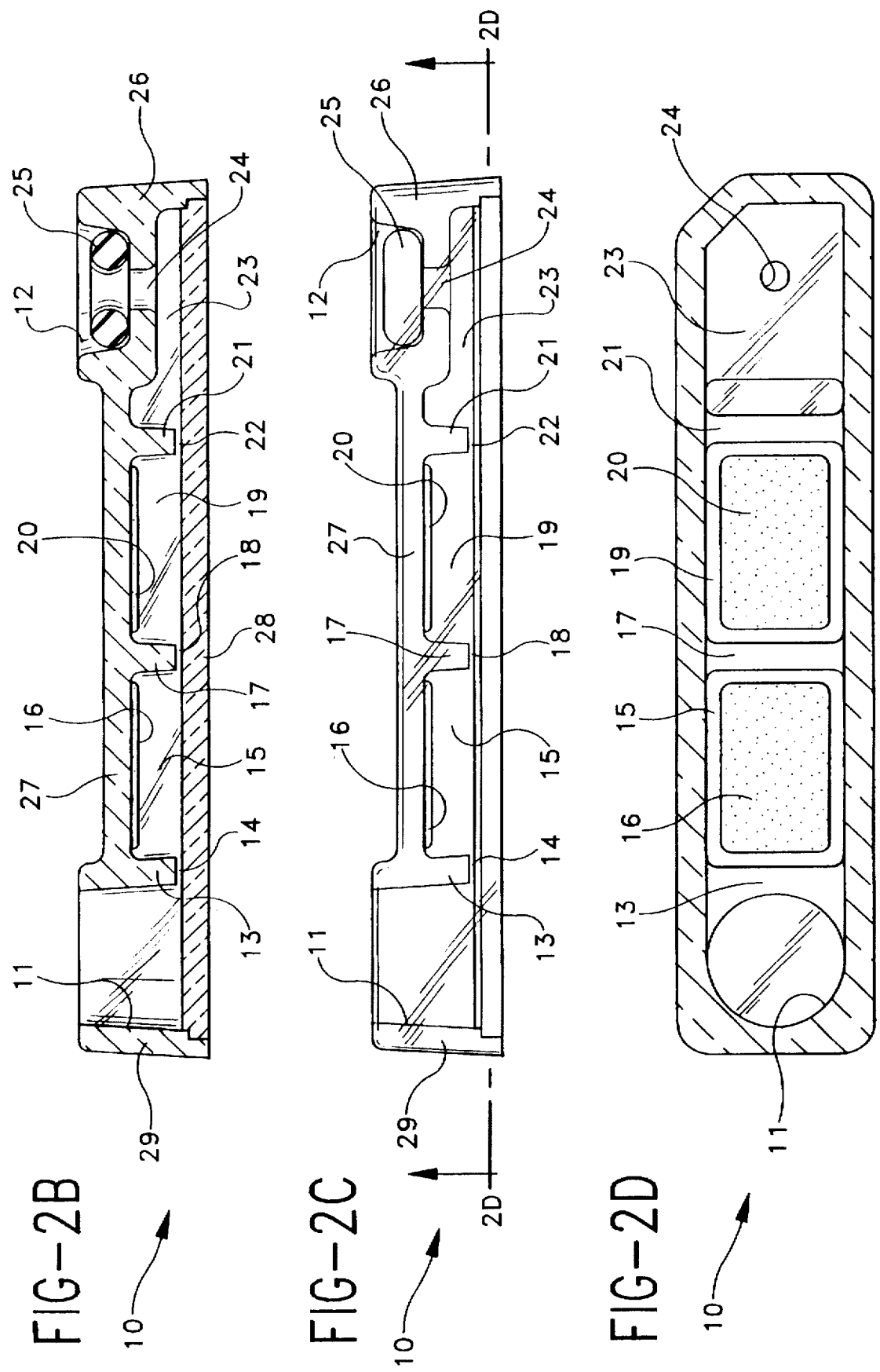

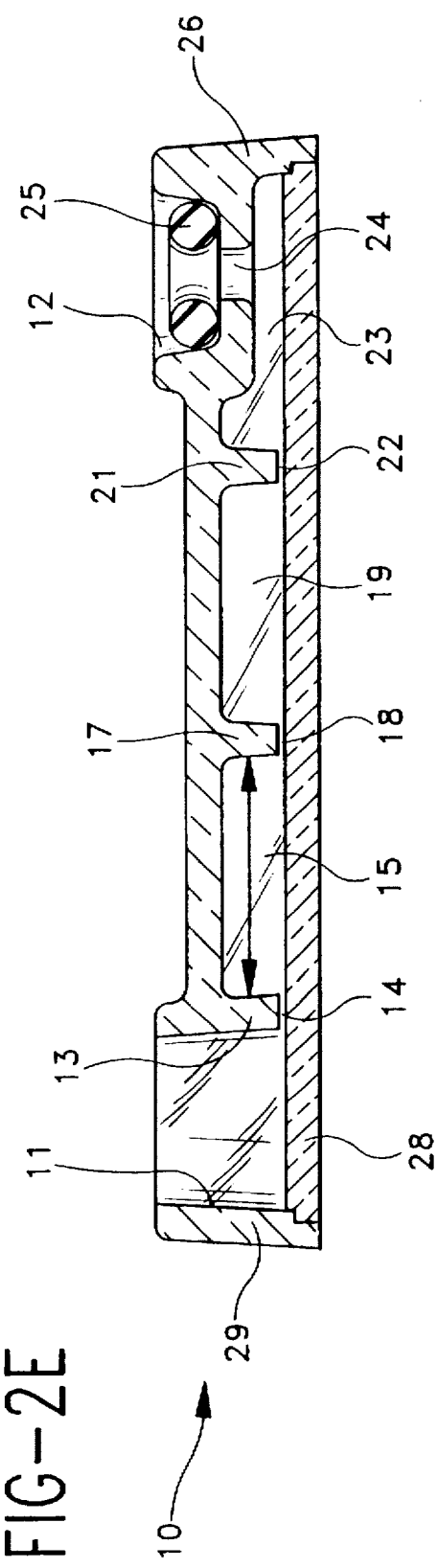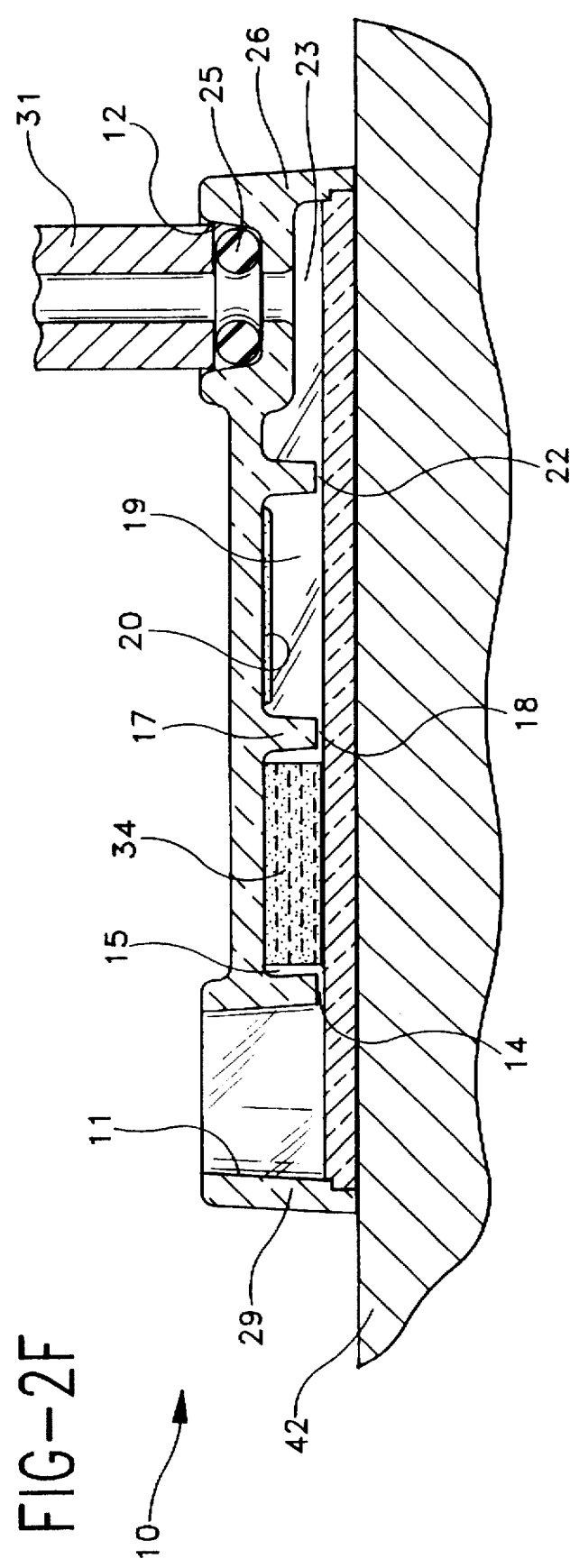

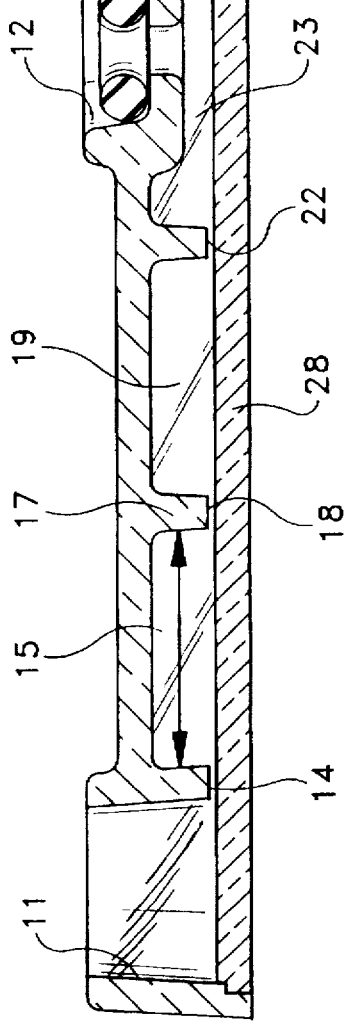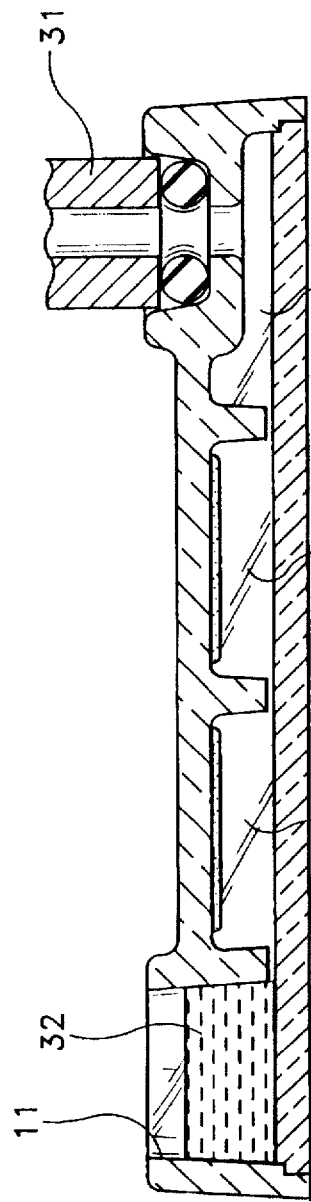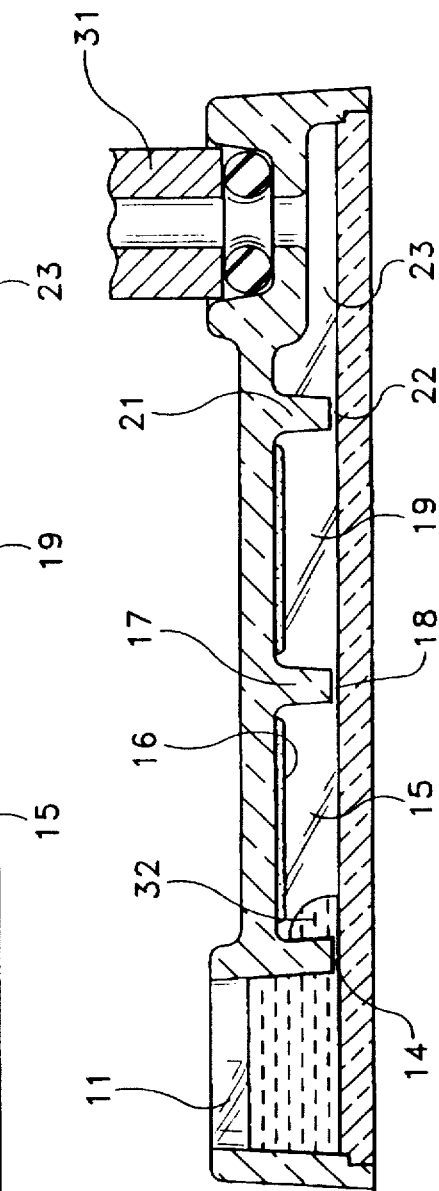
FIG-3A
FIG-3B
FIG-3C

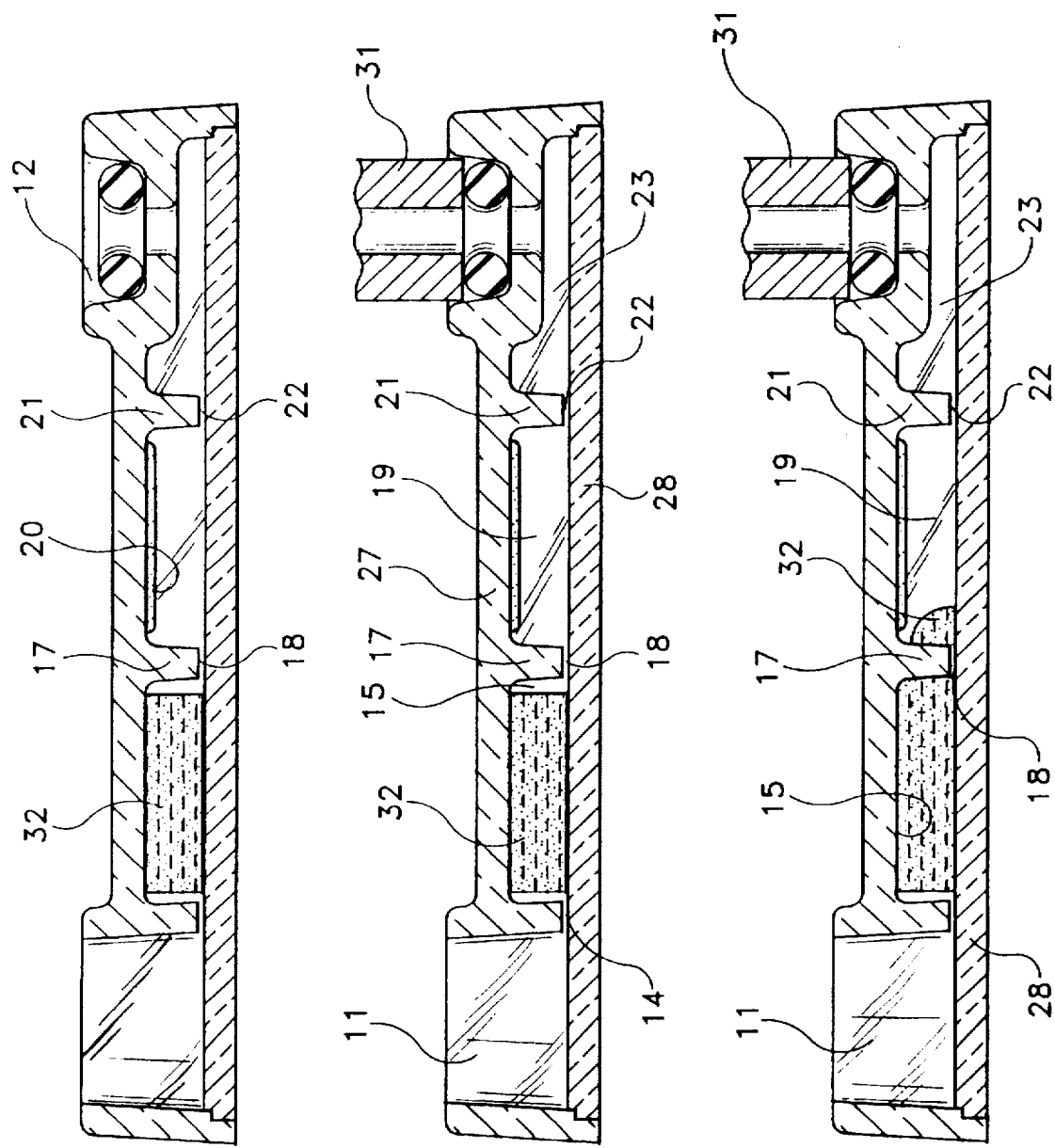

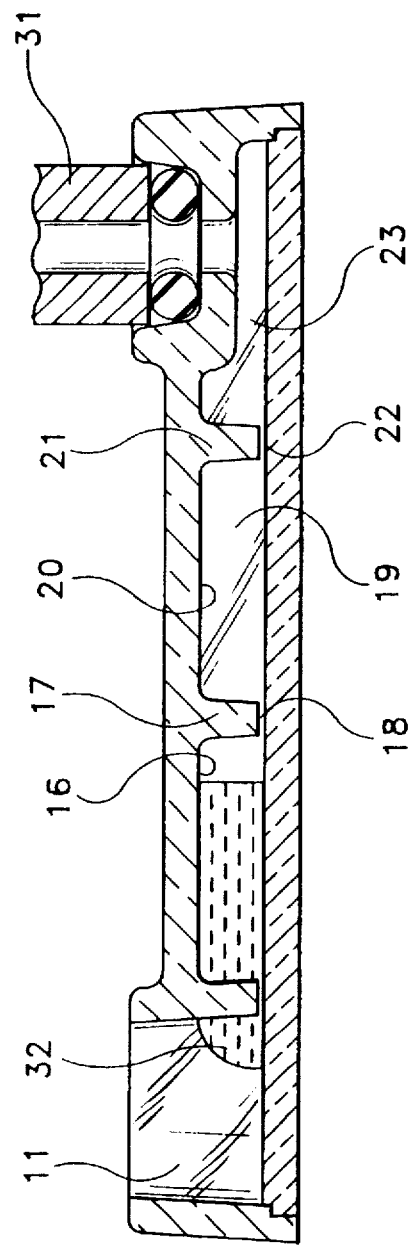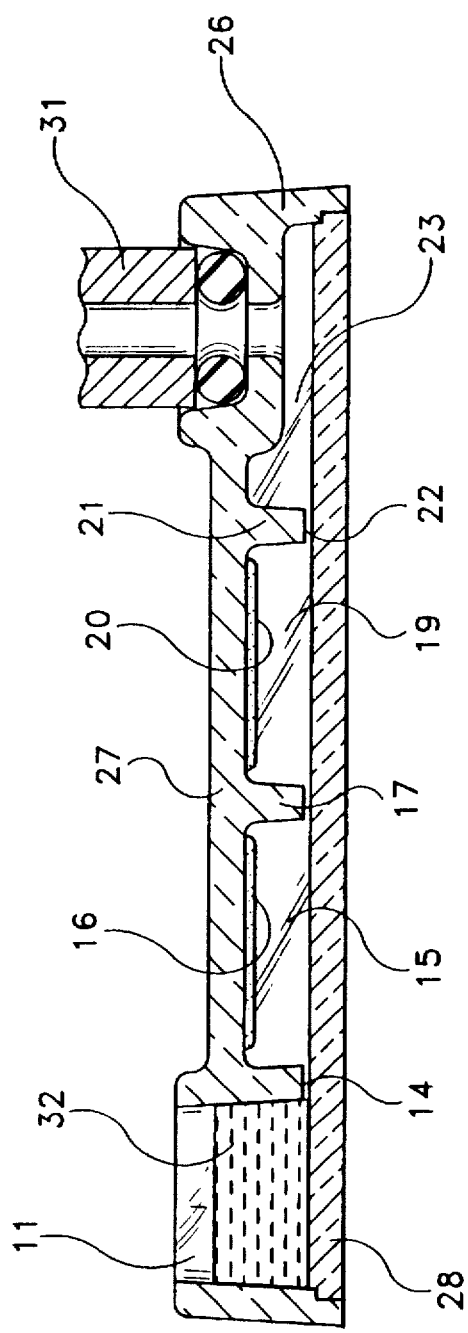

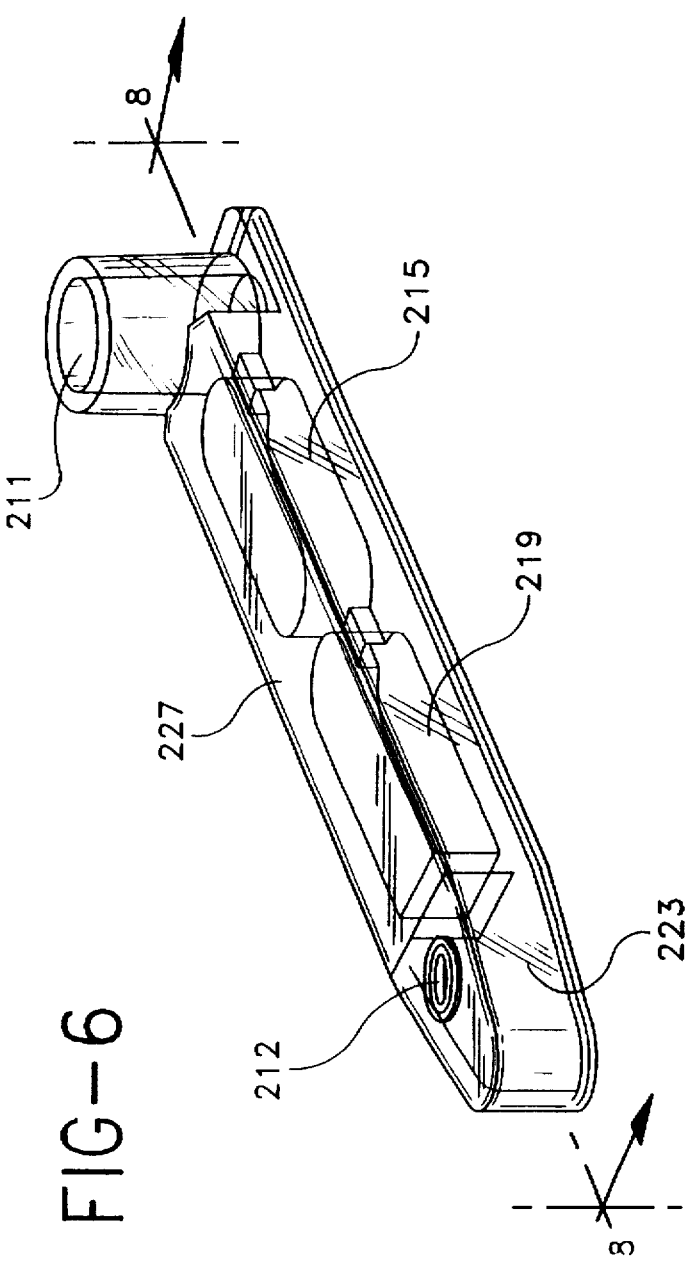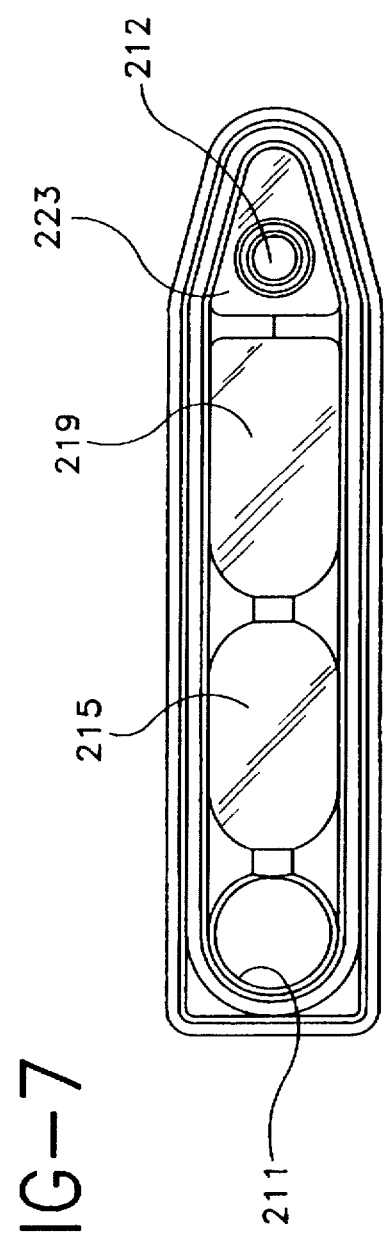

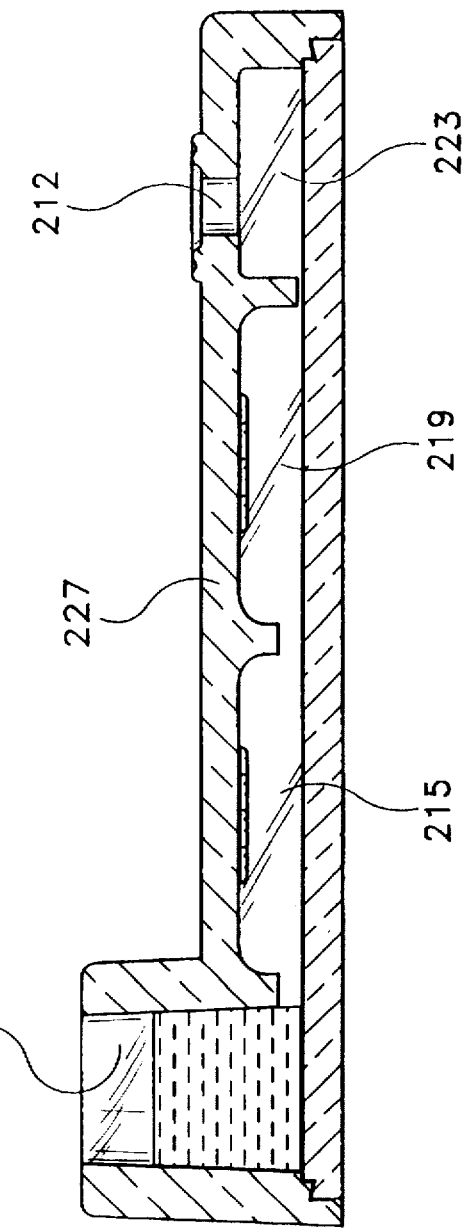
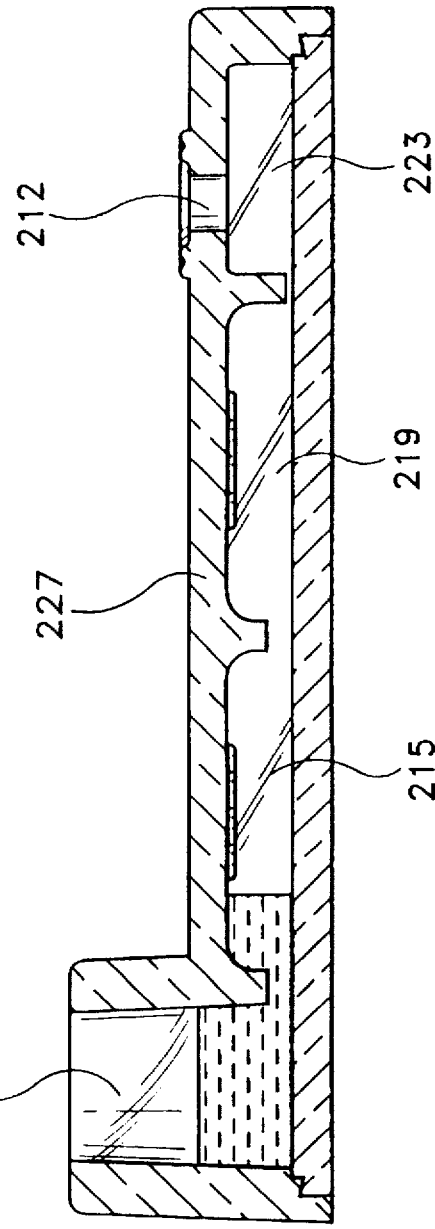

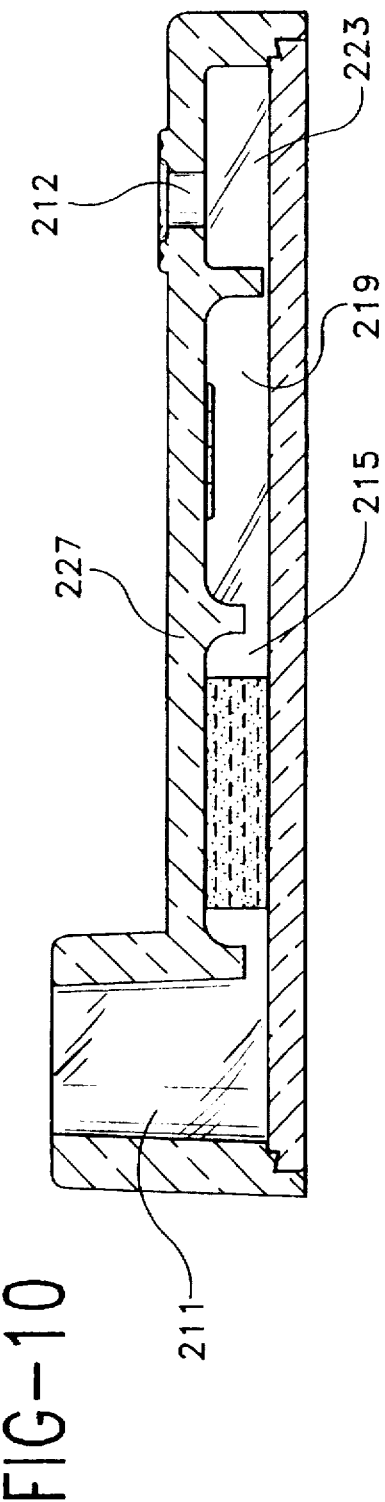
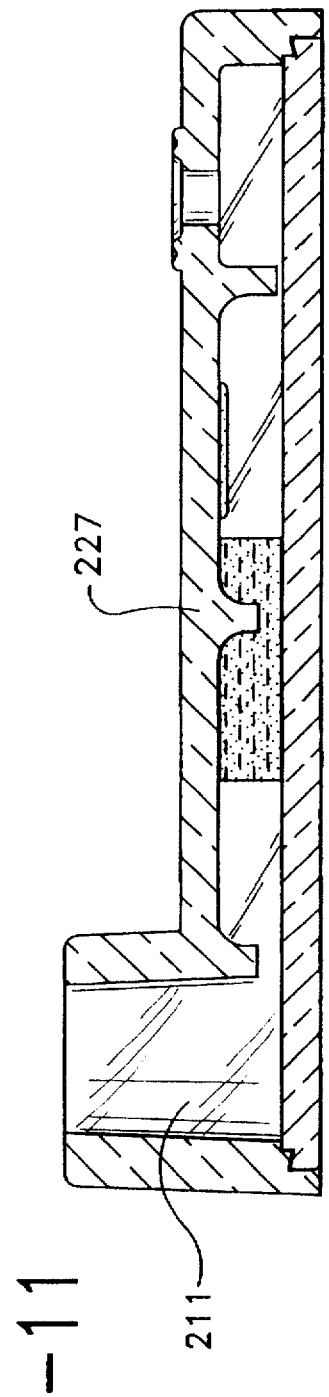
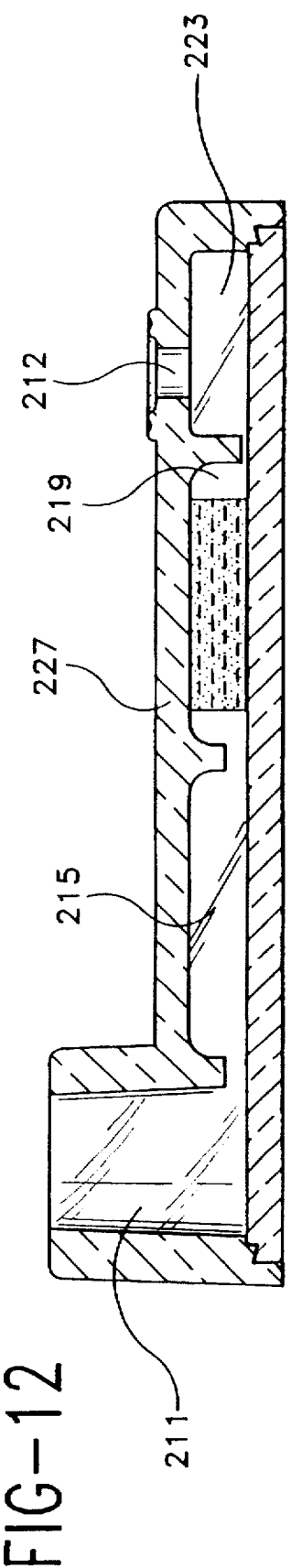
FIG-10
FIG-11
FIG-12

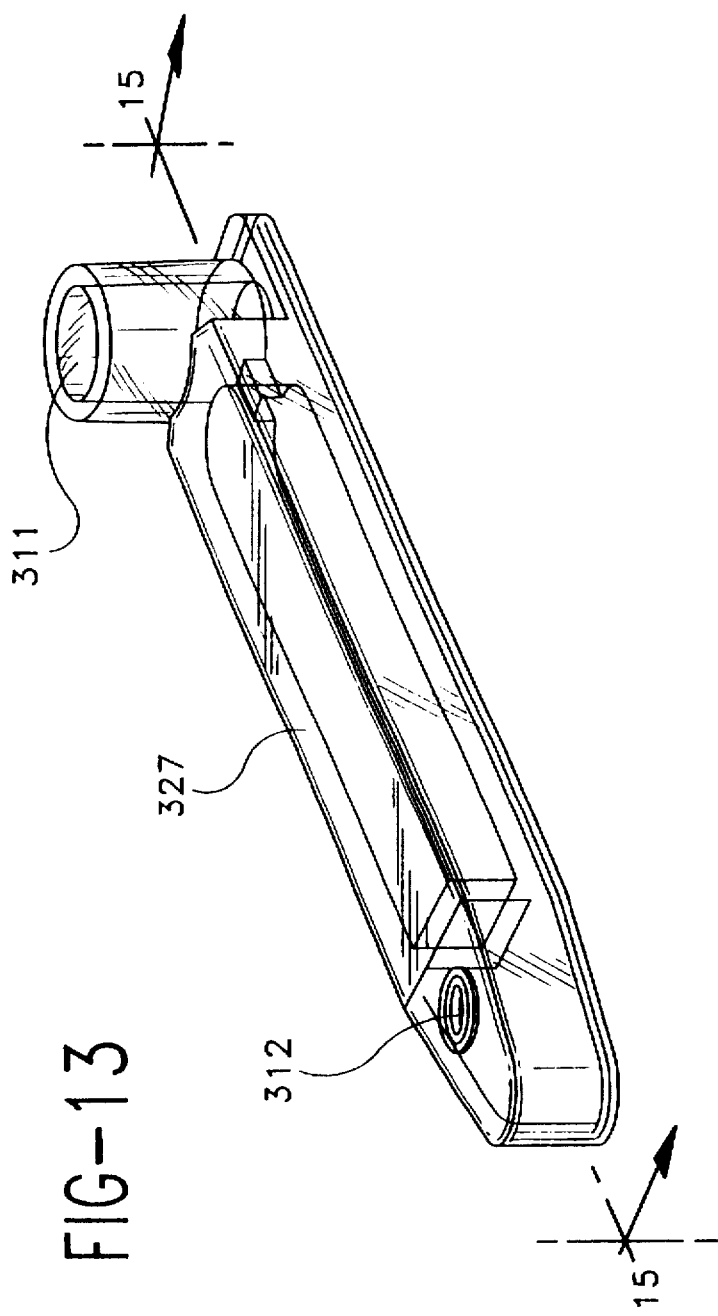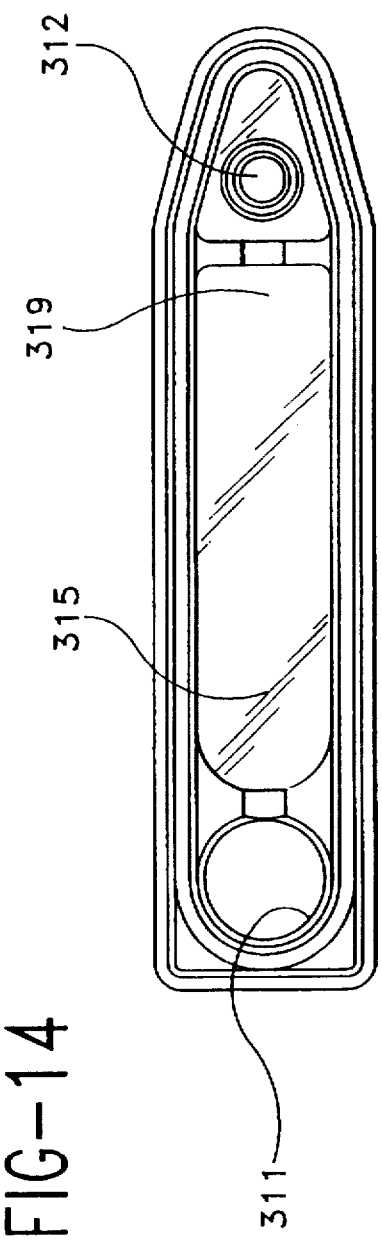

NUCLEIC ACID AMPLIFICATION METHOD AND APPARATUS

This application is a continuation of application Ser. No. 08/213,304, filed Mar. 14, 1994, now abandoned.

FIELD OF THE INVENTION

The present invention relates to an apparatus useful for carrying out a biological process such as nucleic acid amplification, and particularly relates to a unitary apparatus or module useful for carrying out a biological process including a decontamination step in which contaminating amplicons are removed or destroyed and an amplification step in which the number of target nucleic acid segments is increased.

BACKGROUND OF THE INVENTION

Biological processes are often utilized in clinical diagnostic assays. However, the steps of the processes frequently are conducted in different areas of the laboratory and/or in different vessels or containers thereby necessitating transport of biological samples and reagents and giving rise to increased risk of contamination of other clinical samples.

This risk of contamination is of particular concern when the process includes nucleic acid amplification reactions such as strand displacement amplification (SDA) or polymerase chain reaction (PCR) which are capable of multiplying a single strand of nucleic acid (target nucleic acid) into millions of copies (amplicons). While of tremendous potential utility in the clinical diagnostic laboratory, nucleic acid amplification reactions can, however, easily become contaminated with the amplification products (amplicons) of previous amplification reactions. Such contaminating amplicons can in turn contaminate new samples entering the lab, leading to a false positive indication of the substrate to be detected in the contaminated sample (e.g., an incorrect diagnosis).

The problem of amplicon contamination has led to the development of a number of decontamination techniques. In order to be effective, these decontamination techniques generally require that the decontamination step of the process occur prior to the amplification step thereby greatly decreasing the possibility that a contaminating amplicon will be recognized as target nucleic acid during the amplification step.

Decontamination reagents and amplification reagents are often not compatible with each other and may require their own reaction conditions. Sometimes, if the reagents for decontamination and amplification are combined they inactivate each other. Furthermore, performing the decontamination reaction in one container and transfering the decontaminated sample to another container for amplification is not a viable option as there is a high probability that the sample would become recontaminated during the transfer.

In view of the foregoing, a first object of the present invention is to provide methods and apparatus for carrying out one or more biological processes in a single apparatus wherein the processes may necessarily be mutually exclusive.

A second object of the present invention is to provide techniques for carrying out biological processes which include decontamination and amplification of nucleic acid samples in which necessary reagents are contained in a single apparatus.

A still further object of the present invention is to provide an apparatus, in the form of a single unitary module, which can be used to expedite biological processes which include nucleic acid decontamination and amplification reactions.

SUMMARY OF THE INVENTION

In order to address problems associated with contamination of samples, reagents, and products of biological processes, the present invention relates to an apparatus for performing a biological process, which includes: (a) a sample well for introduction and removal of a liquid biological sample; (b) at least one reaction chamber in fluid communication with the sample well; (c) a pneumatic chamber in pneumatic communication with the reaction chamber and sample well; and (d) a pneumatic port in the pneumatic chamber for connection of the apparatus to an pneumatic aspiration/pneumatic dispensing means which causes the flow of liquid biological sample between the sample well and the reaction chamber. The apparatus is generally elongate in shape with the sample well and pneumatic port at opposite ends and the reaction chamber therebetween. Reagents necessary for the biological process are affixed to separate, discrete locations within the reaction chamber.

BRIEF DESCRIPTION OF THE DRAWINGS

The various objects, advantages and novel features of the invention will be more readily appreciated from the following detailed description when read in conjunction with the appended figures, in which:

FIG. 1 is an isometric view of one embodiment of the apparatus of the present invention;

FIG. 2A is a top plan view of the apparatus of FIG. 1;

FIG. 2B is a side sectional view of the apparatus of FIG. 2A taken at line 2B—2B of FIG. 2A;

FIG. 2C is a side view of the apparatus of FIG. 1;

FIG. 2D is a bottom sectional view of the apparatus of FIG. 2C taken at line 2D—2D of FIG. 2C;

FIG. 2E is a side sectional view essentially like FIG. 2B, and detailing length (L) and height (H);

FIG. 2F is a side sectional view of an apparatus essentially like FIG. 2B, and illustrating the module during operation on a heater platen in cooperation with a pipette as an aspiration/dispensing means;

FIGS. 3A–3E are a series of side sectional views taken at line 2B—2B of FIG. 2A showing liquid nucleic acid sample, and the flow of the liquid nucleic acid sample from the sample well to the decontamination area;

FIGS. 4A–4E are a series of side sectional views similar to FIGS. 3A–3E, showing the flow of the liquid nucleic acid sample from the decontamination area to the amplification area; and FIGS. 5A–5E are a series of side sectional views similar to FIGS. 3A–3E, depicting the reverse of the flow of the amplified liquid nucleic acid sample from the amplification area back through the decontamination area to the sample well;

FIG. 6 is an isometric view of another embodiment of the apparatus of the present invention;

FIG. 7 is a top plan view of the apparatus of FIG. 6;

FIG. 8 is a side sectional view of the apparatus of FIG. 6 taken at line 8—8 of FIG. 6;

FIGS. 9–12 are a series of side sectional views taken at line 8—8 of FIG. 6 showing liquid nucleic acid sample, and flow of the liquid nucleic acid sample from the sample well to the decontamination area, and then from the decontamination area to the amplification area;

FIG. 13 is an isometric view of another embodiment of the apparatus of the present invention;

FIG. 14 is a top plan view of the apparatus of FIG. 13;

DETAILED DESCRIPTION OF THE INVENTION

Figure 3D:
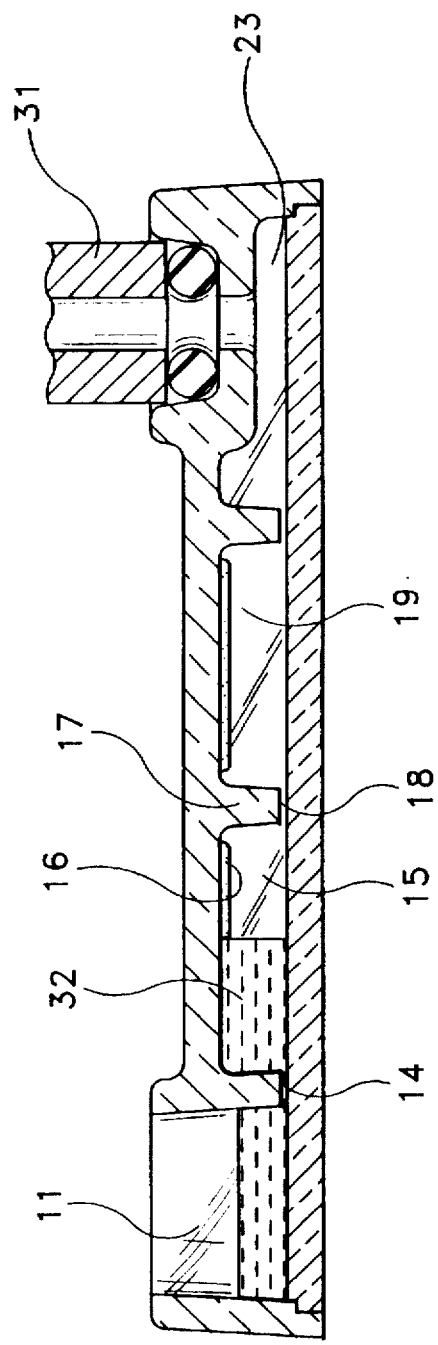

As noted above, the present invention provides methods and apparatus for carrying out a biological process. In overview, one embodiment of the present invention provides for an apparatus which has a sample well, and at least one chamber formed therein. The chamber is in fluid communication with the sample well. The steps of the biological process may be performed at different sites or areas within the chamber.

In an alternative embodiment there are multiple chambers in the apparatus to accommodate the respective multiple steps of the biological process. In one alternative embodiment adopted for use with biological process including a decontamination step and an amplification step, a decontamination area is in fluid communication with the sample well and an amplification area is in fluid communication with the decontamination area. Amplicon decontamination reagents are present in the decontamination area, and nucleic acid amplification reagents are present in the amplification area.

In use, a liquid sample containing nucleic acid is moved from the sample well into the decontamination area where the liquid sample contacts the decontamination reagents and amplicons in the sample are degraded. The liquid sample is then moved from the decontamination area to the amplification area where the liquid sample contacts the amplification reagents and amplicons are thus generated in the sample. The liquid sample is then dispensed from the amplification area, through the decontamination area to the sample well. Moving and withdrawing of the sample may be carried out by any suitable pneumatic means.

Once the sample is withdrawn, the presence of amplicons in the sample can be detected by any suitable means, such as with nucleic acid probes which bind to the amplicons, which probes are labeled with detectable groups (e.g., enzymes, radioisotopes, etc.), all in accordance with known techniques. Alternatively, the apparatus may be configured to allow detection steps to be carried out in situ by inclusion of additional areas and reagents in the apparatus.

An isometric view of one specific embodiment of the apparatus of the present invention is shown in FIG. 1. This is a multi-chambered embodiment which is shaped approximately as a rectangular prism, and has nominal dimensions of about 1.370 inches in length, about 0.304 inches in width and about 0.200 inches in height. A sample well (11) with a diameter of about 0.214 inches and a depth of about 0.160 inches, for the receipt of about 75 μL of the liquid biological sample, is at one end and is open at the top surface of the apparatus to receive the sample to be processed. As will be recognized by those skilled in the art, the dimensions of the apparatus need not be specifically as set forth above, and may be varied substantially provided that the apparatus continues to function adequately as a closed apparatus for performance of the desired biological process. However, a general guideline for variance of the dimensions is to maintain approximately the same ratios between dimensions as are presented by the specified dimensions above. At the end opposite to the sample well (11) is a pneumatic port (12) having a diameter of approximately 0.185 inches. The pneumatic port is also open at the top surface of the apparatus (10).

Referring to FIGS. 2A and 2B, FIG. 2B is a magnified, sectional view of the apparatus (10) taken at line 2B—2B of FIG. 2A. Sample well (11) is defined by walls (29) and (13) and bottom (28). This sample well (11) communicates with decontamination area (15) by a first microchannel (14) created by the virtual abutment of wall (13) to apparatus bottom (28). The gap between wall (13) and apparatus bottom (28), which creates the first microchannel (14), in this specific embodiment is about 0.006 inches in height and exists across the entire internal width of the apparatus (10). An alternate embodiment of the apparatus has a domed microchannel with a greater height and smaller width (i.e. generally, the shape of an inverted "U"). Microchannel sizes and shapes are dependent on the viscosity and surface tension of the fluid to be moved through the apparatus.

A decontamination area (15) is defined by walls (13) and (17), top (27) and apparatus bottom (28). In this specific embodiment of the present invention, the decontamination area is about 0.315 inches in length, about 0.222 inches in width, and about 0.080 inches in height. The decontamination area has a volume of about 90 μL. As was discussed above, the dimensions of the decontamination area, like the dimensions of the apparatus, may be varied considerably provided that the decontamination step functions properly. However, a general guideline for varying dimensions is to maintain the ratios between dimensions which are presented by the specified dimensions above.

Contained within the decontamination area are the nucleic acid decontamination reagents necessary for the decontamination reaction. The decontamination reagents, (the necessary active ingredients for the decontamination reaction as described above), may be those required for any suitable means of decontamination. The decontamination reagents may be in any suitable form, including but not limited to a solid such as a dried film, lyophilized pellets or paper impregnated with the reagent.

In a preferred embodiment of the present invention, the decontamination reagents (16) are disposed upon (i.e., adhered to) the inner surface of the top (27), in dried form. FIG. 2D, which is a magnified sectional view taken at line 2D—2D of FIG. 2C further shows the location of dried chemical decontamination reagents (16) within the area (15) and apparatus (10). The preferred method for drying the decontamination reagents is to dry the reagents in the presence of trehalose as taught in U.S. Pat. No. 4,891,319 and Patent Cooperation Treaty International Publication No. WO 87/00196, both publications owned by Quadrant Bioresources Limited and both publications incorporated herein by reference. Briefly, the preferred drying technique protects biological materials against denaturation during drying, and involves subjecting an aqueous system containing the biological material to a temperature above freezing in the presence of trehalose in an amount between about 0.05 and 20 weight percent based on the total weight of the aqueous system. Trehalose is a naturally occurring non-reducing disaccharide also known as α-D-glucopyranosyl-α-D-gluco-pyranoside.

The drying in the presence of trehalose may be simple air drying, preferably at atmospheric pressure. In the drying of the decontamination and amplification reagents, trehalose increases chemical stability of the reagents significantly. Thus, the trehalose technology is an excellent system for drying any reagents to be used in the apparatus.

The decontamination area (15) communicates with an amplification area (19) by a second microchannel (18) created by the virtual abutment of wall (17) to the apparatus bottom (28). As with the first microchannel, in this specific embodiment the gap between wall (17) and apparatus bottom (28) creates a second microchannel (18) which is about 0.006 inches in height and exists across the entire internal width of the apparatus (10). However, as was true for the first microchannel, an alternative embodiment has a domed microchannel with a greater height and smaller width.

The amplification area (19) is defined by walls (17) and (21), top (27) and apparatus bottom (28). As was true for the decontamination area, in this specific embodiment, the amplification area is about 0.315 inches in length, about 0.222 inches in width, about 0.080 inches in height and has a volume of about 90 µL. However, these dimensions may be varied in accordance with the same guidelines set forth above for variance of the dimensions of the decontamination area.

Contained within the amplification area are the reagents necessary for the amplification reaction. The amplification reagents are those active agents required for any suitable nucleic acid amplification reaction, as described above. In a preferred embodiment of the present invention, the amplification method used is Strand Displacement Amplification. The amplification reagents, like the decontamination reagents, may be in any suitable form, including but not limited to a solid such as a dried film, lyophilized pellets, or paper impregnated with the reagents. The amplification reagent may optionally include active agents such as a probe necessary for detection of the amplicon to be generated, as discussed above, particularly where detection is to be carried out in situ. Of course, the amplification reagent need not be provided in the same form as the decontamination reagent.

In a preferred embodiment of the present invention, the amplification reagent or reagents (20) are disposed upon the inner surface of the top (27), in dried form. FIG. 2D shows the location of dried chemical amplification reagents (20) within the chamber (19) of a preferred embodiment. The trehalose technology preferred for drying of the decontamination reagents is also preferred for drying of the amplification reagents.

The amplification area (19) communicates with a pneumatic chamber (23) by a third microchannel (22) created by the virtual abutment of wall (21) to the apparatus bottom (28). As with the first and second microchannels, in this specific embodiment the gap between wall (21) and module bottom (28), which creates a third microchannel (22), is about 0.006 inches and exists across the entire internal width of the apparatus (10).

The pneumatic chamber (23) is defined by walls (21) and (26), pneumatic port (12) and apparatus bottom (28). In the preferred embodiment of the present invention, the pneumatic chamber is about 0.315 inches in length, about 0.222 inches in width, and as shown in FIG. 2B, varies from about 0.080 inches to about 0.040 inches in height. The pneumatic chamber is about 55 µL in volume. As was true for the dimensions of the decontamination area and the amplification area, the dimensions of the pneumatic chamber may also be varied in accordance with the same guidelines set forth above for variance of the dimensions of the decontamination and amplification areas. The pneumatic chamber (23) communicates with pneumatic port (12) by hole (24) and through the center of a sealing mechanism (25) such as an "O" ring or other means to the top surface of the apparatus (10) at the pneumatic port (12).

The geometric form of the apparatus of FIG. 1 and the material that it is composed of generate intrinsic forces which control the liquid biological sample within the apparatus. In this embodiment, all surfaces in contact with the liquid sample have a contact angle between the apparatus and the liquid biological sample of about greater than or equal to 90 degrees. Having a contact angle of about greater than or equal to 90 degrees is often referred to as a non-wettable surface. Liquid flow within the apparatus due to capillary and hydrostatic forces is essentially eliminated by the non-wettable surfaces within the apparatus combined with the sharp increase in height between the microchannels and the reaction chambers (from about 0.006 inches in the microchannel to about 0.080 inches in the chambers in a preferred embodiment). The apparatus thus exhibits several discrete zones which trap liquid.

The form factor of the microchannels and the reaction chambers substantially decreases the trapping of air at the top of the reaction chambers and also insures that the liquid sample develops a rectilinear profile which contributes to discrete, accurate and predictable positioning within the apparatus. Referring to FIG. 2E, the length (L) between wall (13) and wall (17) of the decontamination area (15), should be greater than the height (H) between apparatus bottom (28) and top (27). The same ratio of length to height is also desirable for the amplification area (19). This form factor (L>H), insures that air is not trapped at the top of the decontamination area (15) or amplification area (19) and therefore the various reagents in these chambers are fully exposed to the liquid sample.

The form (length>height) and location of the microchannels function to reduce evaporative loss of the liquid biological sample. FIGS. 2B and 2F show the form and location of the microchannels (14), (18), (22) and their relation to the liquid sample (34), here shown in the decontamination area (15). In this embodiment the microchannels have a height of about 0.006 inches formed by their respective walls (13), (17), (21). These walls have a thickness dimension of about 0.040 inches but can vary between about 0.030 and about 0.060 inches. The microchannels (14), (18), (22) therefore exhibit a length that is greater than their height. This ratio (L>H) reduces the rate of evaporation of the liquid sample out of either the decontamination area (15) or the amplification area (19). The microchannel location, at the bottom of the decontamination area (15) and the amplification area (19), further reduces the rate of evaporation of the liquid sample.

A second embodiment of the apparatus of the present invention is shown in isometric view in FIG. 6. As with the first embodiment of the invention, this second embodiment is a multi-chambered embodiment which is shaped approximately as a rectangular prism and has nominal dimensions which are the same as those for the first embodiment. The sample well (211) also has similar diameters and volume as that in the first embodiment and is used for the same purpose. At the opposite end of the sample well (211) is a pneumatic port (212) with a similar diameter to that of the first embodiment of the invention.

The primary difference between the first and second embodiments of the present invention can be seen in FIG. 7, which shows an increased radius for the corners of the decontamination area (215) and the amplification area (219).

As can be seen in FIG. 7, all of the interior corners of the decontamination area (216) have an increased radius and the corners of the amplification area (219) which are closest to the decontamination area have an increased radius. An increase in the radius of the corners improves the fluid flow from one area to another in the apparatus. Optimally, the fluid flows as an undivided unit from one area to another within the apparatus as shown in FIGS. 9–11. It was found that the increase in radius of the corners improved this fluid flow feature. The degree of radiusing is that which is sufficient to permit the fluid to move from those corners with the bulk of the liquid sample. Optimal radiusing is about a 0.040 inch radius. In contrast, the radiusing of the corner of the first embodiment is about 0.015 inch.

Another feature which improved the fluid flow from one area of the apparatus to another was the use of the domed microchannel with a greater height and smaller width. This channel configuration is utilized between the sample well (211) and the decontamination area (215) as well as between the decontamination area (215) and the amplification area (219). Since the fluid does not flow between the amplification area (219) and the pneumatic chamber (223), the microchannel between these two areas of the apparatus need not be domed.

The other features of this second embodiment of the invention are very similar if not virtually identical to the features of the first embodiment of the invention. Similarly, the dimensions of various aspects of this second embodiment of the invention are again very similar if not virtually identical to the dimensions of the first embodiment. Also, the reagents used for decontamination and amplification are disposed upon the inner surface of the top (227) of the apparatus in dried form.

Figure 16:
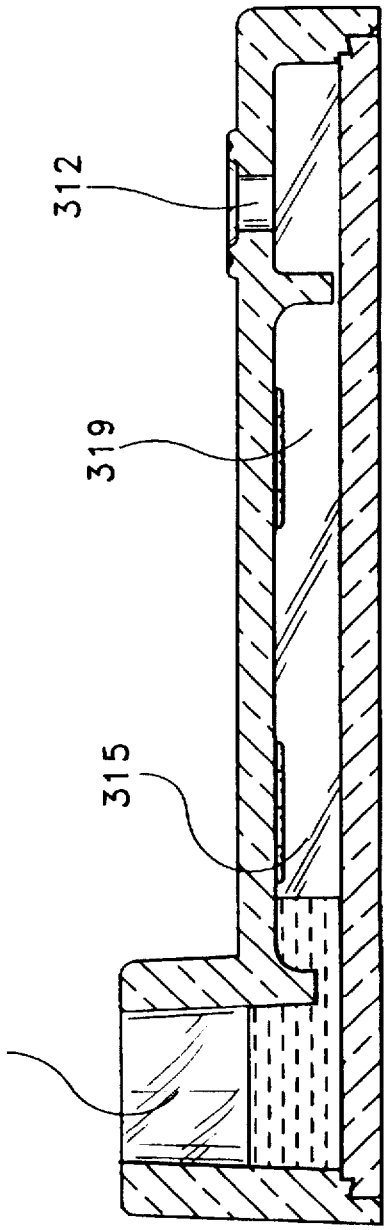
FIGS. 16–18 are a series of side sectional views taken at line 15—15 of FIG. 13 showing liquid nucleic acid sample, and the flow of the liquid nucleic acid sample from the sample well to the decontamination area, and from the decontamination area to the amplification area.
Figure 17:
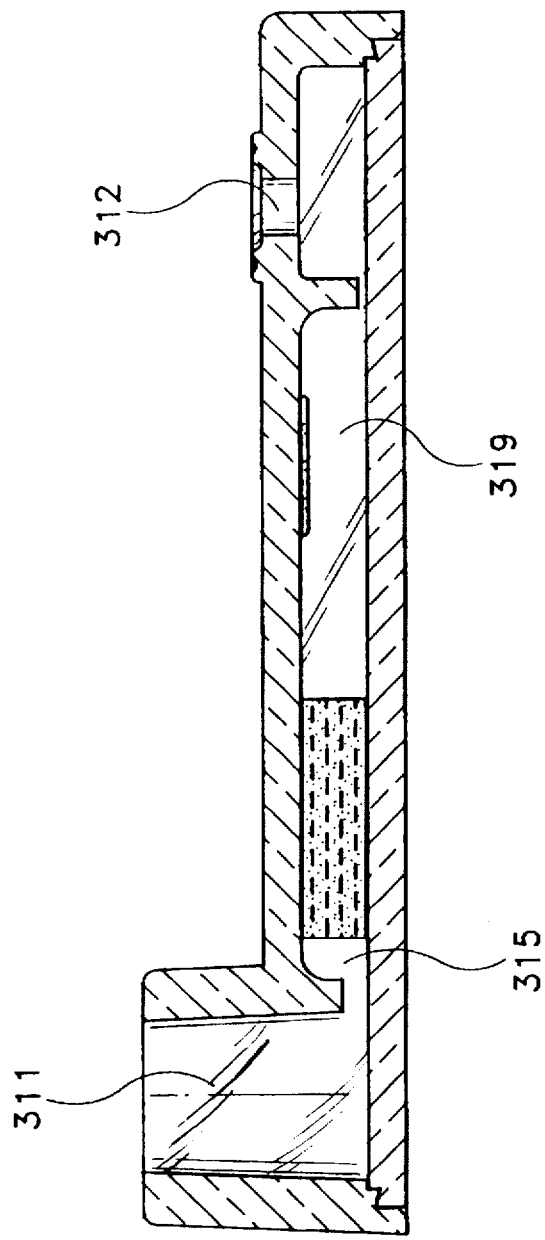
Figure 18:
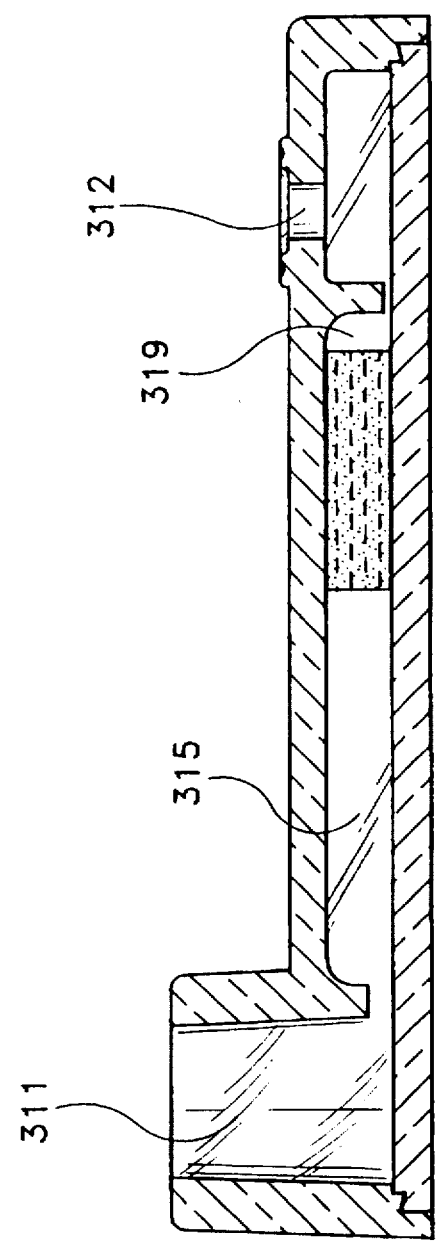

A third embodiment of the present invention is shown in isometric view in FIG. 13. The distinguishing feature of this embodiment of the invention is that there is no wall or microchannel between the decontamination area (315) and the amplification area (319) of the apparatus. As shown in FIGS. 16–18, it was found that the liquid sample could be moved from one area to another within the chamber as a single undivided unit. Thus, decontamination reagents are disposed upon the top (327) of the apparatus in an area closer to the sample well, while amplification reagents are disposed upon the top (327) of the apparatus in an area which is more removed from the sample well (311) and closer to the pneumatic port (312). Again, in order to optimize the flow of liquid sample as a undivided unit in the chamber, the interior corners of the chamber closest to the sample well (311) are radiused as they were in the second embodiment of the present invention. As with the second embodiment of the invention, the degree of curvature of the radiused corners must be sufficient to permit the fluid to move from those corners with the bulk of the sample as pneumatic pressure is applied to the liquid sample. Thus, it is found that the optimal radiusing of corners is about 0.040 inch. As with the second embodiment of the invention, the third embodiment of the invention has very similar if not virtually identical features and dimensions to the first embodiment of the invention other than the absence of the wall and microchannel between the decontamination area (315) and the amplification area (319) of the apparatus.

The apparatus of the present invention may be conveniently constructed of any suitable plastic and by any suitable plastic processing method, either as a single part or as multiple parts for subsequent assembly. Such materials and methods include but are not limited to thermoplastic polymers molded using conventional molding techniques such as injection molding. Exemplary thermoplastic polymers include polypropylenes, polymethylpentene, and copolymers and mixtures thereof.

The apparatus of the present invention is preferably produced from polypropylene plastic injection molded to form two parts: apparatus top and apparatus bottom (28). The apparatus top is inverted and reagents necessary for amplification (20) and decontamination (16) are dried as films onto the inner top surface of the amplification area (19) and decontamination area (15), respectively. Subsequently, the apparatus bottom (28) is ultrasonically welded onto the apparatus top, forming a single unit.

The apparatus of the present invention allows different thermal environments to exist therewithin, thereby permitting the use of reagents requiring different reaction temperatures. The apparatus may be positioned upon a heating platen (42) during the entire time of its operation. This heating platen can be controlled to any suitable temperature, typically 20° C.–100° C. Depending upon the actual reagents, the decontamination reaction may require a temperature that would destroy the amplification reagents in the amplification area. As shown in FIG. 2F (which depicts a multiple chamber embodiment during the decontamination reaction), the heating platen (42) is in direct contact with the apparatus bottom (28), which is in direct contact with liquid sample (34). After a suitable period of time, the liquid sample (34) will reach thermal equilibrium and be approximately similar in temperature to the temperature of the heating platen (42). During this time, however, the amplification area (19) is not filled with the liquid sample but with air. Air has a thermal conductivity that is about 25 times lower than the liquid sample. For this reason the air in the amplification area acts as a thermal insulator between the apparatus bottom (28) and the amplification reagents (20). This prevents the amplification reagents (20) from being exposed to a temperature which could destroy them. After the decontamination reaction is completed, the temperature of the heating platen (42) can be changed to one which is compatible with the amplification reagents, and the liquid sample (34), after equilibrating to this new temperature, can be moved into the amplification area (19) by pipette (31) or other suitable pneumatic means or aspirating/dispensing means which may be operated manually or by robotics. The reverse of the above description, in which the decontamination reagents cannot withstand a temperature that the amplification reagents require, is also accommodated by the present invention. Furthermore, these same thermal principles are applicable to a single chamber embodiment where liquid is present in one area of the chamber and air is in the other areas of the chamber.

In the present invention, the liquid sample is confined in the chamber or chambers such that there is preferably no head space. Head space refers to the space filled with air above a liquid in a container. Head space is often not desirable in systems that require a liquid to undergo a chemical reaction at a uniform temperature, as the head space allows a portion of the liquid to condense on the walls and top of the container and to exist at a different temperature than the bulk of the liquid. By being at a different temperature, some chemical reactions are not completed properly. In the case of the amplification of a liquid sample, this usually means reduced amplification. As shown in FIG. 2F, the liquid sample (34) fully contacts the top of the decontamination area and has virtually no head space. Similarly, in a preferred embodiment the liquid sample fully contacts the top of the amplification area.

When used for the performance of biological processes including an amplification step, one of the primary functions of the apparatus is to provide an environment which is free of contaminating amplicons. In addition to liquid nucleic acid samples that contain contaminating nucleic acids, contact of a sample with contaminated items is a major mode of amplicon contamination. In a laboratory that is performing nucleic acid amplification, everything is a potential means of amplicon contamination. The apparatus physically isolates the amplification environment within the amplification area. The design of the apparatus contains no moving parts that could be opened at anytime, and therefore never exposes the amplification area to the amplicon contaminated external environment. Internal contact of the sample within the amplification area is prevented by the decontamination area (15) and pneumatic chamber (23) on either side, and by their microchannel access.

The air flow through the apparatus of the present invention is designed to minimize aerosol amplicon contamination caused by the pipette or other pneumatic means. During the various stages before amplification the pipette only moves air from the apparatus. The pipette does not dispense air into the apparatus. In this way, amplicons which may be contaminating the pipette are drawn away from the amplification area.

Once amplification has occurred, the direction of air flow is reversed. Now the pipette only dispenses air into the apparatus. In this way, amplicons in the amplification area flow away from the pipette, reducing the possibility of aerosol amplicon contamination of the pipette. The amplified liquid sample is returned to the sample well (11) of the apparatus and can be removed for subsequent nucleic acid probe assay.

The specific form factor of the apparatus of the present invention allows an array of apparati to be reacted simultaneously, and their final amplified output can be automatically transferred to a nucleic acid probe assay without operator intervention.

The flow of the liquid nucleic acid sample within the first embodiment of apparatus (e.g. FIGS. 1 and 2) is shown in FIGS. 3A–3E, FIGS. 4A–4E, and FIGS. 5A–5E. However, the same principles and descriptions of the flow are substantially similar for the other illustrated embodiments of the present invention.

FIG. 3A shows the initial empty state of the apparatus. (For reasons of clarity, the heater platen, upon which the module is positioned during typical operation, is deleted in these figures. Refer to FIG. 2F to see the apparatus in a view representative of typical operation including the heating platen (42)).

FIG. 3B shows the liquid sample (34) in the sample well and the tip of a pipette (31) engaged in the pneumatic port of the apparatus. The non-wettable property and the form of the apparatus prevents the liquid sample from passing through the microchannel out of the sample well.

FIG. 3C shows the liquid sample as it is being initially aspirated by the pipette into the decontamination area of the apparatus. The spherical profile (32) of the liquid sample is generated by the surface tension of the film in conjunction with the perpendicular walls.

FIG. 3D shows the liquid sample being aspirated still further into the decontamination area.

Figure 3E:
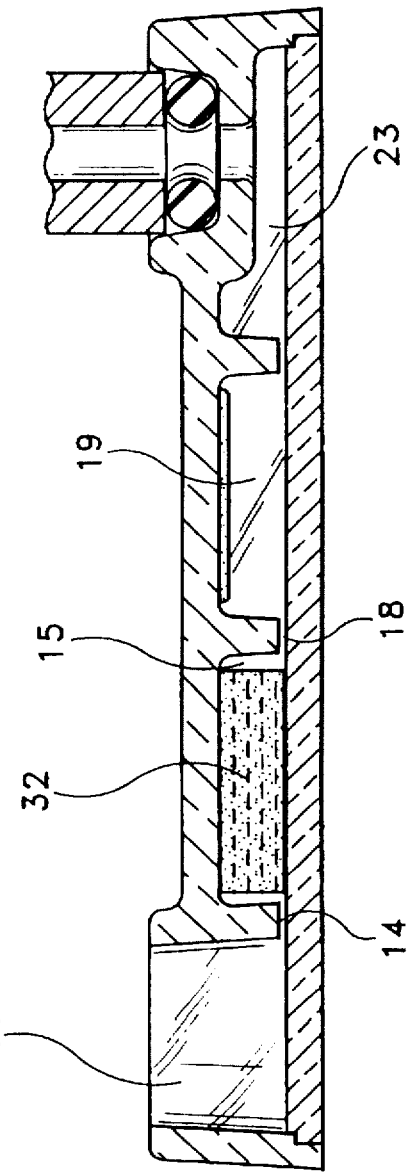
Figure 4D:
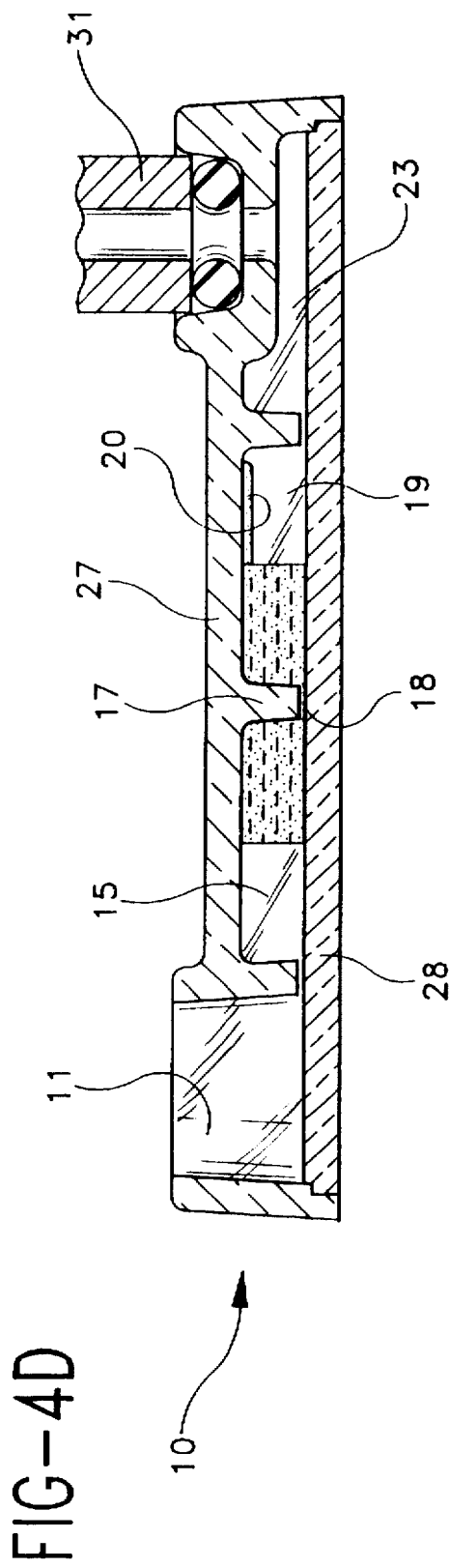
Figure 4E:
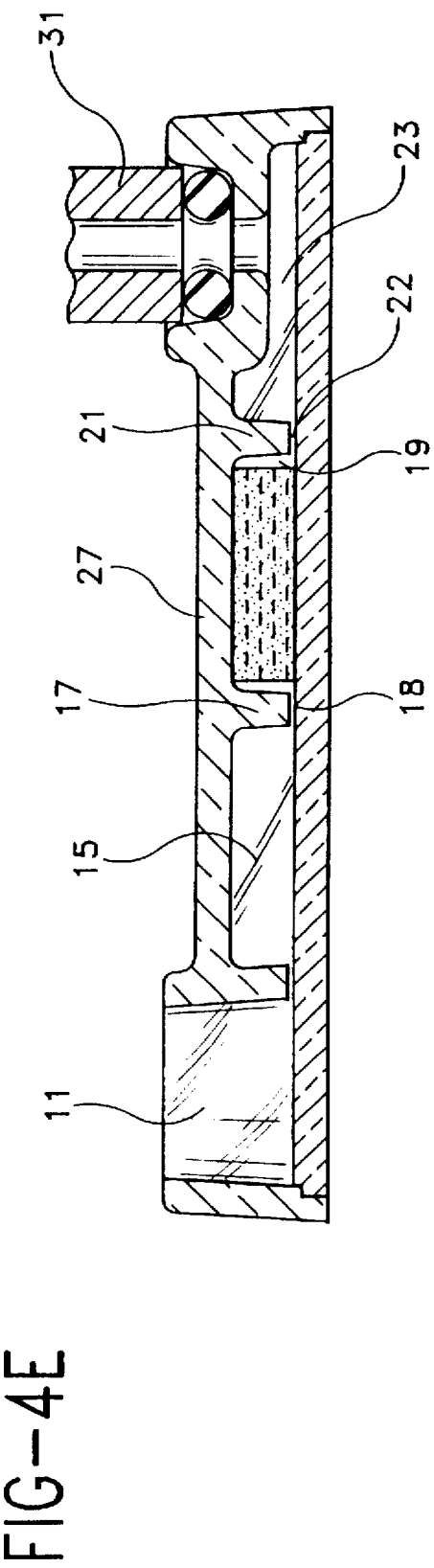

FIG. 3E shows the liquid sample (34) fully positioned within the decontamination area. The reagents are completely contacted (covered) by the liquid sample and both profiles of the liquid surface tension films are rectilinear.

FIG. 4A shows the liquid sample (34) during decontamination. The pipette has been disengaged from the apparatus and is not needed until decontamination is completed and movement of the liquid sample to the next area is required. Alternatively, the pipette need not be disengaged provided that aspiration does not take place until decontamination is completed.

FIGS. 4B–4E show the return of the engagement of the pipette to the apparatus and the movement of the liquid sample (34) from the decontamination area into the amplification area.

Figures 5A, 5B, 5C:
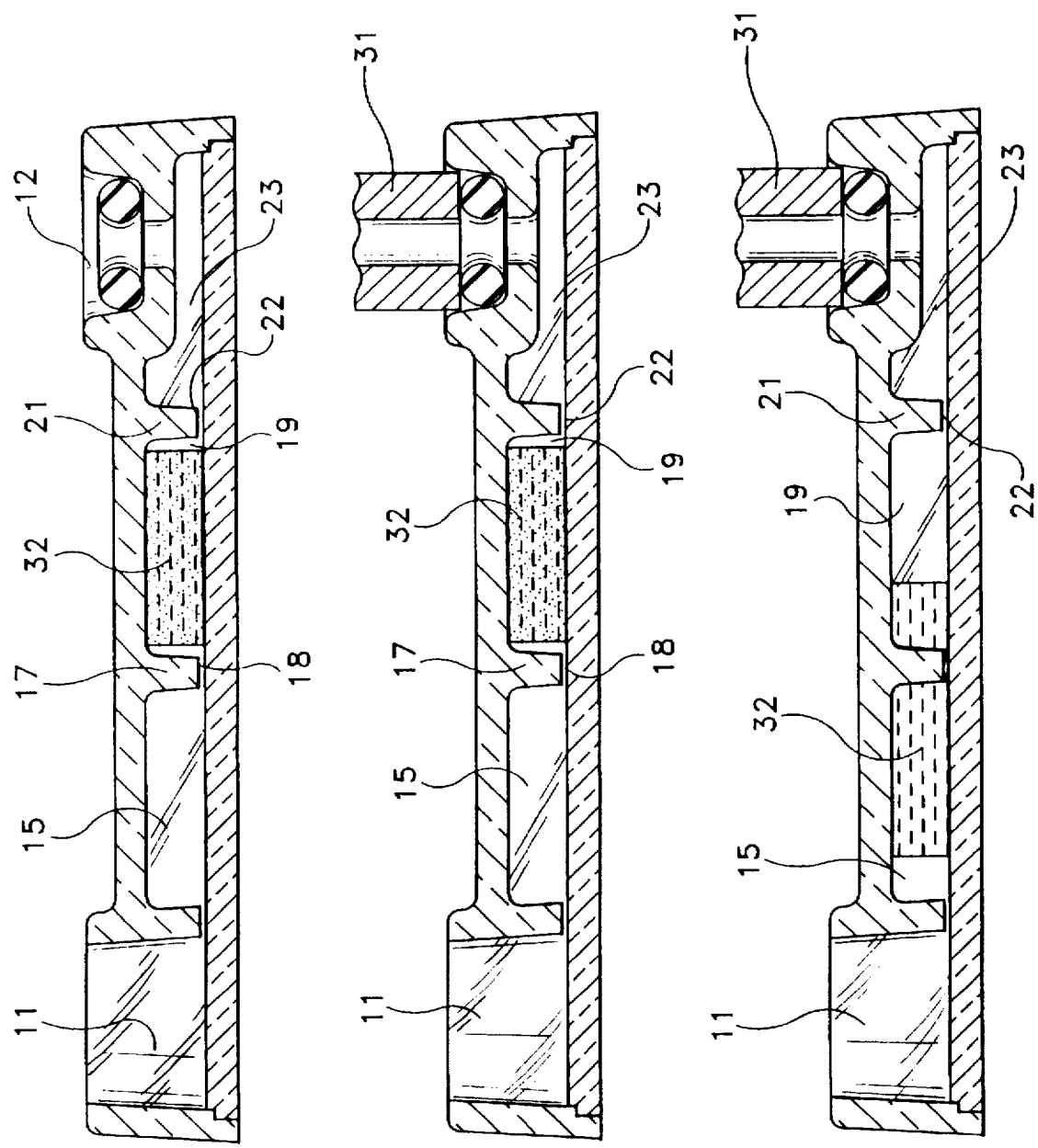
Figure 15:
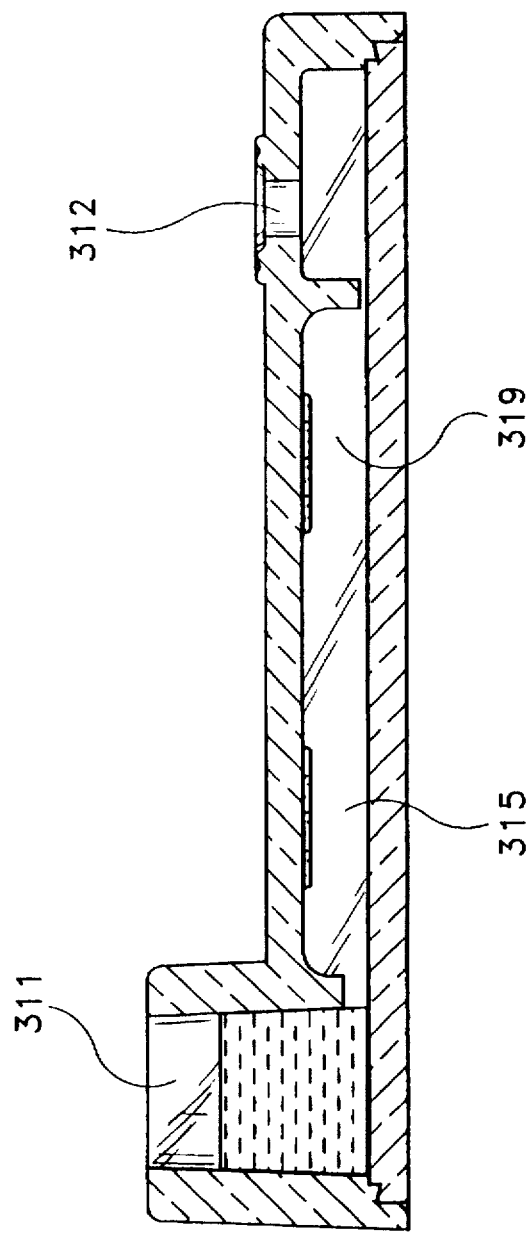
FIG. 15 is a side sectional view of the apparatus of FIG. 13 taken at line 15—15 of FIG. 13.

FIG. 5A shows the liquid sample (34) during amplification. Again the pipette has disengaged from the apparatus and is not needed until amplification is completed and movement of the liquid sample is required. However, as with the decontamination step, the pipette need not be disengaged provided that pneumatic dispensing does not take place until amplification is completed.

FIGS. 5B–5E show the return of the engagement of the pipette (31) to the apparatus and the reversal of the movement of the liquid sample (34) back through the decontamination area to the sample well. The reversal of flow is achieved through the dispensing of air by the pipette into the apparatus. In the preferred embodiment, in order to move the amplified sample all the way back to the sample well, the pipette would dispense a volume of air equal to or greater than the total volume of the decontamination and amplification areas combined, or in the specifically exemplified embodiment, about greater than or equal to 180 µL. Typically this volume might be 200 µL.

In general, the liquid sample employed in the present invention will be an aqueous preparation containing the target nucleic acid (i.e., ribonucleic acid (RNA), deoxyribonucleic acid (DNA)) and any contaminating amplicons, with either (or both) the target nucleic acid and the amplicons in single-stranded form. For example, the target nucleic acid may comprise randomly sheared genomic DNA fragments. The preparation will be in a form suitable for use in a nucleic acid amplification procedure, in accordance with known techniques. Target nucleic acid will typically comprise nucleic acid fragments of from about 5,000 nucleotides in length to about 200,000 nucleotides in length (with lengths representing an average of the lengths found in the preparation). Within the target nucleic acid is the sequence of interest to be amplified. The sequences for amplification can range from as few as ten base pairs to several thousand, with base pairs of about 15 to about 200 preferred.

The length of amplicons to be degraded by the method of the present invention will vary depending upon the particular nucleic acid amplification method by which the amplicons are produced, but will usually be at least about 25 nucleotides in length, and typically will be not more than about 2,000 nucleotides in length. When the amplicons are produced by Strand Displacement Amplification (SDA), they will typically be not more than about 200 nucleotides in length.

Decontamination to remove contaminating amplicons in a sample containing target nucleic acid sequence may be carried out by any suitable means, including using double strand specific exonucleases and single strand specific exonucleases. Hence, decontamination reagents may contain one or more single strand or double strand specific exonuclease. For example, R. Griffis, PCT Application WO 91/00363 (published 10 Jan. 1991) discloses a method of decontaminating a PCR reaction product with a 5' lambda exonuclease. Similarly, Y. S. Zhu et al., *Nucleic Acids Res.* 19, 2511 (1991), disclose the use of exonuclease III for removing amplicons from a PCR reaction product. Both the lambda exonuclease and exonuclease III are double-strand specific exonucleases. Any single strand-specific exonuclease can be employed in carrying out the present invention so long as it is capable of degrading the amplicons. Examples of suitable single-strand specific exonucleases include, but are not limited to, exonuclease VII (see, e.g., J. Chase and C. Richardson, *J. Biol. Chem.* 249, 4545–4552 (1974); J. Chase and C. Richardson, *J. Biol. Chem.* 249, 4553–4561 (1974)), exonuclease I (see, e.g., R. Brody, *Biochemistry* 30, 7072–7080 (1991)), Pfu DNA polymerase from *Pyrococcus furiosus* (Stratagene, LaJolla, Calif.), DNA polymerase I from *Escherichia coli*, klenow fragment from DNA polymerase I of *E. coli*, T7 DNA polymerase, T4 DNA polymerase, spleen exonuclease (*J. Biol Chem.* 253: 424 (1978), T5 D15 Exonuclease (*Nucleic Acids Research* 19:4127 (1991), "Vent" DNA polymerase from *Thermococcus litoralis* (New England Biolabs, Beverly, Mass.), and DNA polymerases which have 3'-5' exonuclease activity. DNA polymerases having 3'-5' exonuclease activity employed in carrying out the invention should be capable of degrading phosphorothioate linkages if the amplicons to be degraded are the products of SDA. See generally F. Eckstein, *Ann. Rev. Biochem.* 54, 367–402 (1985)(3'-5' exonuclease activity of T4 DNA polymerase can cleave phosphorothioate DNA but that from *E. coli* DNA polymerase I can not). It will be appreciated that the exonuclease need only degrade the amplicons sufficiently so that the amplicons will not serve as a substrate for a subsequent nucleic acid amplification reaction (i.e., produce a false positive result from a nucleic acid preparation which would not otherwise serve as a substrate for the amplification reaction but for contamination by the amplicons).

Alternatively, the decontamination step of the process may be performed using the techniques taught in U.S. Pat. No. 5,035,996 or published European Patent Application No.0 415 755 A2, both of which are incorporated herein by reference. These patent publications are owned by Life Technologies Inc. and describe decontamination techniques wherein one of the four normal ribonucleotides or deoxyribonucleotides used in the amplification procedure is replaced with an exo-sample nucleotide. Then, after amplification, any amplicons which may contaminate another sample are subjected to a physical, chemical, enzymatic, or biological treatment to render the amplicons containing the exo-sample nucleotide substantially unamplifiable. A preferred exo-sample nucleotide is deoxyuridine (dUTP) when the target nucleic acid is DNA. When dUTP is utilized as the exo-sample nucleotide, the contaminating amplicons are subjected to enzymatic treatment with uracil DNA glycosylase (UDG) to render the amplicons unamplifiable.

Amplification of a selected, or target, nucleic acid sequence may be carried out by any suitable means. See generally D. Kwoh and T. Kwoh, *Am. Biotechnol. Lab.* 8, 14–25 (1990). Examples of suitable amplification techniques include, but are not limited to, polymerase chain reaction (PCR), ligase chain reaction (LCR), Strand Displacement Amplification (SDA), transcription-based amplification (see D. Kwoh et al., *Proc. Natl. Acad Sci. USA* 86, 1173–1177 (1989)), self-sustained sequence replication (or "3SR")(see J. Guatelli et al., *Proc. Natl. Acad. Sci. USA* 87, 1874–1878 (1990)), the Qβ replicase system (see P. Lizardi et al., *Bio Technology* 6, 1197–1202 (1988)), nucleic acid sequence-based amplification (or "NASBA")(see R. Lewis, *Genetic Engineering News* 12 (9), 1 (1992)), the repair chain reaction (or "RCR")(see R. Lewis, supra), and boomerang DNA amplification (or "BDA")(see R. Lewis, supra). Strand Displacement Amplification (or "SDA"), is preferred.

Strand Displacement Amplification may be carried out in accordance with known techniques. See generally G. Walker et al., *Proc. Natl. Acad. Sci. USA* 89, 392–396 (1992); G. Walker et al., *Nucleic Acids Res.* 20, 1691–1696 (1992). For example, SDA may be carried out with a single amplification primer or a pair of amplification primers, with exponential amplification being achieved with the latter. In general, SDA amplification primers comprise, in the 5' to 3' direction, a flanking sequence (the DNA sequence of which is noncritical), a restriction site for the restriction enzyme employed in the reaction, and an oligonucleotide sequence which hybridizes to the target sequence to be amplified and/or detected. The flanking sequence, which serves to facilitate binding of the restriction enzyme to the recognition site and provides a DNA polymerase priming site after the restriction site has been nicked, is preferably about 15 to 20 nucleotides in length; the restriction site is functional in the SDA reaction (i.e., phosphorothioate linkages incorporated into the primer strand do not inhibit subsequent nicking—a condition which may be satisfied through use of a nonpalindromic recognition site); the oligonucleotide probe portion is preferably about 13 to 15 nucleotides in length.

SDA is carried out with a single amplification primer as follows: a restriction fragment (preferably about 50 to 100 nucleotides in length and preferably of low GC content) containing the sequence to be detected is prepared by digesting a DNA sample with one or more restriction enzymes, the SDA amplification primer is added to a reaction mixture containing the restriction fragment so that a duplex between the restriction fragment and the amplification primer is formed with a 5' overhang at each end, a restriction enzyme which binds to the restriction site on the amplification probe (e.g., HincII) is added to the reaction mixture, an exonuclease deficient DNA polymerase (e.g., an exonuclease deficient form of *E. coli* DNA polymerase I, see V. Derbyshire, *Science* 240, 199–201 (1988)) is added to the reaction mixture, and three dNTPs and one dNTP[S], with the dNTP[S] selected so that a phosphorothioate linkage is incorporated into the primer strand at the restriction site for the particular restriction enzyme employed (e.g., dGTP, dCTP, dTTP, and dATP[S] when the restriction enzyme is HincII) are added to the reaction mixture. The DNA polymerase extends the 3' ends of the duplex with the dNTPs to form a downstream complement of the target strand. The restriction enzyme nicks the restriction site on the amplification primer, and the DNA polymerase extends the 3' end of the amplification primer at the nick to displace the previously formed downstream complement of the target strand. The process is inherently repetitive because the restriction enzyme continuously nicks new complementary strands as they are formed from the restriction site, and the DNA polymerase continuously forms new complementary strands from the nicked restriction site.

SDA can also be carried out with a pair of primers on a double stranded target DNA sequence, with the second primer binding to the 3' end of the complementary strand, so that two sets of repetitive reactions are occurring simultaneously, with the process proceeding exponentially because the products of one set of reactions serve as a target for the amplification primer in the other set of reactions.

The step of first digesting the DNA sample to form a restriction fragment in an SDA reaction can be eliminated by exploiting the strand displacing activity of the DNA polymerase and adding a pair of "bumper" primers which bind to the substrate at a flanking position 5' to the position at which each amplification primer binds. Each bumper primer extension product displaces the corresponding amplification primer extension product. Amplification primers, which are present in excess, then bind to the displaced primer extension products, and upon extension, a double-stranded DNA fragment is formed which can then serve as a substrate for exponential SDA with that pair of amplification primers.

Polymerase chain reaction (PCR) may also be carried out in accordance with known techniques. See, e.g., U.S. Pat. Nos. 4,683,195; 4,683,202; 4,800,159; and 4,965,188 (the disclosure of all U.S. Patent references cited herein are to be incorporated herein by reference). In general, PCR involves, first, treating a nucleic acid sample (e.g., in the presence of a heat stable DNA polymerase) with one oligonucleotide primer for each strand of the specific sequence to be detected under hybridizing conditions so that an extension product of each primer is synthesized which is complementary to each nucleic acid strand, with the primers sufficiently complementary to each strand of the specific sequence to hybridize therewith so that the extension product synthesized from each primer, when it is separated from its complement, can serve as a template for synthesis of the extension product of the other primer, and then heating the sample to separate the primer extension products from their templates if the sequence or sequences to be detected are present. These steps are continued cyclically, preferably in a thermal cycler, until the desired degree of amplification is obtained. Detection of the amplified sequence may be carried out by adding to the reaction product an oligonucleotide probe capable of hybridizing to the reaction product (e.g., an oligonucleotide probe of the present invention), the probe carrying a detectable label, and then detecting the label in accordance with known techniques.

Ligase chain reaction (LCR) is also carried out in accordance with known techniques. See, e.g., R. Weiss, *Science* 254, 1292 (1991). In general, the reaction is carried out with two pairs of oligonucleotide probes: one pair binds to one strand of the sequence to be detected; the other pair binds to the other strand of the sequence to be detected. Each pair together completely overlaps the strand to which it corresponds. The reaction is carried out by, first, denaturing (e.g., separating) the strands of the sequence to be detected, then reacting the strands with the two pairs of oligonucleotide probes in the presence of a heat stable ligase so that each pair of oligonucleotide probes is ligated together, then separating the reaction product, and then cyclically repeating the process until the sequence has been amplified to the desired degree. Detection may then be carried out in like manner as described above with respect to PCR.

The foregoing is illustrative of the present invention, and is not to be construed as limiting thereof, as numerous alternatives to those methods and devices described above which incorporate the present invention will be apparent to those skilled in the art. The invention is accordingly defined by the following claims, with equivalents of the claims to be included therein.

That which is claimed is:

1. An apparatus for performing a biological process on a liquid biological sample using reagents, comprising:
    (a) a sample well for introduction and removal of a liquid biological sample;
    (b) at least one reaction chamber wherein reagents for the biological process are affixed at discrete locations therein, said reaction chamber in fluid communication with the sample well and being constructed to permit the liquid biological sample to move sequentially between said locations as a discrete bolus in response to an applied pneumatic force, said bolus remaining stationary in the absence of an applied pneumatic force without appreciable sample movement as a result of capillary force;
    (c) a pneumatic chamber in pneumatic communication with the reaction chamber and sample well; and
    (d) a pneumatic port in the pneumatic chamber for connection of the apparatus to a pneumatic aspiration/dispensing means, said aspiration/dispensing means providing said pneumatic force to cause the movement of said liquid biological sample between the sample well and the reaction chamber and between said locations in said reaction chamber.

2. The apparatus of claim 1 wherein said apparatus is elongate in shape with the sample well and the pneumatic port formed at opposite ends thereof, and the reaction chamber positioned therebetween.

3. The apparatus of claim 2 wherein the interior corners of a wall of the reaction chamber which is a common wall of the sample well are radiused.

4. The apparatus of claim 1 further comprising a liquid flow control means positioned between the sample well and the reaction chamber.

5. The apparatus of claim 4 wherein the liquid flow control means comprises a microchannel.

6. The apparatus of claim 5 wherein the microchannel is configured to substantially prevent liquid flow by hydrostatic force therethrough.

7. The apparatus of claim 1, wherein said apparatus is formed from non-wettable material.

8. The apparatus of claim 7 wherein said apparatus is formed from polypropylene.

9. The apparatus of claim 7 wherein said apparatus is formed from polymethylpentene.

10. The apparatus of claim 1 wherein the biological process performed comprises a nucleic acid decontamination/amplification process which produces nucleic acid amplicons, said decontamination/amplification process including a decontamination step to remove contaminating amplicons from said liquid biological sample and a nucleic acid amplification step to produce new amplicons of a target nucleic acid sequence in the decontaminated sample, and wherein said reagents are those necessary for said decontamination and amplification steps and are disposed on an inner wall of the reaction chamber at different areas such that the biological sample is subjected to the decontamination step prior to the amplification step.

11. The apparatus of claim 10 wherein the process to perform the nucleic acid amplification step is selected from the group consisting of polymerase chain reaction, ligase chain reaction, strand displacement amplification, transcription based amplification, self-sustained sequence replication, Qβ replicase amplification, nucleic acid sequence-based amplification, and repair chain amplification.

12. The apparatus of claim 10 wherein the process to perform the nucleic acid amplification step is strand displacement amplification.

13. The apparatus of claim 12 wherein the reagents necessary for the nucleic acid amplification step comprise strand displacement amplification primers.

14. The apparatus of claim 1 comprising two reaction chambers, a first reaction chamber in direct fluid communication with the sample well and a second reaction chamber in indirect fluid communication with the sample well through said first reaction chamber and in direct pneumatic communication with the pneumatic chamber.

15. The apparatus of claim 14 further comprising liquid flow control means positioned between the sample well and the first reaction chamber and between the first reaction chamber and the second reaction chamber.

16. The apparatus of claim 14 wherein the first reaction chamber and the second reaction chamber are defined by inner walls on which are disposed the dried reagents necessary for performance of the biological process.

17. The apparatus of claim 16 wherein the biological process performed comprises a nucleic acid decontamination/amplification process which produces nucleic acid amplicons, said decontamination/amplification process including a decontamination step to remove contaminating amplicons from said liquid biological sample and a nucleic acid amplification step to produce new amplicons of a target nucleic acid sequence in the decontaminated sample, and wherein those of said reagents necessary for said decontamination step are affixed to an inner wall of the first reaction chamber and those of said reagents necessary for said nucleic acid amplification step are affixed to an inner wall of the second reaction chamber.

18. An apparatus for carrying out nucleic acid decontamination and amplification on a liquid biological sample, comprising:

a sample well for the introduction and removal of a liquid biological sample;

at least one reaction chamber in fluid communication with said sample well, said reaction chamber being constructed to permit the liquid biological sample to move therein as a discrete bolus in response to an applied pneumatic force, said bolus remaining stationary in the absence of an applied pneumatic force without appreciable sample movement as a result of capillary force;

at least one dried nucleic acid decontamination reagent and at least one dried nucleic acid amplification reagent affixed at discrete, spaced-apart locations in said reaction chamber; and a pneumatic port in pneumatic communication with said reaction chamber and said sample well for connecting said apparatus to a pneumatic aspiration and dispensing means, said pneumatic aspiration and dispensing means providing said pneumatic force to move said liquid biological sample between said sample well and said reaction chamber and sequentially between said discrete, spaced-apart locations of said reaction chamber.

19. The apparatus of claim 18, wherein said reaction chamber has an elongated shape with said sample well and said pneumatic port at opposite ends thereof, said dried decontamination reagent being positioned closer to said sample well than said dried amplification reagent in said reaction chamber.

20. The apparatus of claim 18, wherein said apparatus is made of a non-wettable material.

21. The apparatus of claim 18, wherein said dried nucleic acid amplification reagent performs a nucleic acid amplification process selected from the group consisting of polymerase chain reaction, ligase chain reaction, strand displacement amplification, transcription based amplification, self-sustained sequence replication, Qβ replicase amplification, nucleic acid sequence-based amplification, and repair chain amplification.

22. The apparatus of claim 18, further comprising liquid flow control means located between said sample well and said reaction chamber for substantially preventing the flow of said liquid biological sample between said sample well and said reaction chamber in the absence of pneumatic aspiration or dispensing applied through said pneumatic port by said pneumatic aspiration and dispensing means.

23. The apparatus of claim 22, wherein said liquid flow control means comprises a microchannel.

24. The apparatus of claim 18, wherein said pneumatic port faces upwardly to receive a downwardly extending pipette forming a part of said pneumatic aspiration and dispensing means.

25. The apparatus of claim 24, further comprising sealing means surrounding said pneumatic port for forming a pneumatic seal with said pipette.

26. The apparatus of claim 18, further comprising a pneumatic chamber in pneumatic communication with said reaction chamber and said sample well, said pneumatic chamber having said pneumatic port therein.

27. The apparatus of claim 26, further comprising liquid flow control means located between said pneumatic chamber and said reaction chamber for substantially preventing the flow of said liquid biological sample between said reaction chamber and said pneumatic chamber.

28. The apparatus of claim 27, wherein said liquid flow control means comprises a microchannel.

29. The apparatus of claim 28, wherein said apparatus is made of a non-wettable material.

30. The apparatus of claim 18, wherein said reaction chamber is divided into first and second reaction chambers, said first reaction chamber containing said decontamination reagent and being in direct fluid communication with said sample well, and said second reaction chamber containing said amplification reagent and being in fluid communication with said sample well through said first reaction chamber and in pneumatic communication with said pneumatic port.

31. The apparatus of claim 30, wherein said first and second reaction chambers are separated by liquid flow control means which substantially prevents the flow of said liquid biological sample between said first and second reaction chambers in the absence of pneumatic aspiration or dispensing applied through said pneumatic port by said pneumatic aspiration and dispensing means.

32. The apparatus of claim 31, wherein said liquid flow control means comprises a microchannel.

33. The apparatus of claim 32, wherein said apparatus is made of a non-wettable material.

* * * * *